United States Patent [19]

Goetz

[11] 4,239,612

[45] Dec. 16, 1980

[54] AUTOMATIC ELECTROPHORESIS APPARATUS

[75] Inventor: Philip J. Goetz, Pleasantville, N.Y.

[73] Assignee: Pen Kem, Inc., Croton-On-Hudson, N.Y.

[21] Appl. No.: 16,181

[22] Filed: Feb. 28, 1979

Related U.S. Application Data

[62] Division of Ser. No. 767,770, Feb. 11, 1977.

[51] Int. Cl.³ ................ G01N 27/26; G01N 27/28; G01N 27/30
[52] U.S. Cl. .......................... 204/299 R; 204/180 R
[58] Field of Search ........... 204/180 R, 195 T, 195 R, 204/1 R, 299, 300

[56] References Cited

U.S. PATENT DOCUMENTS

| | | | |
|---|---|---|---|
| 2,744,061 | 5/1956 | DeFord et al. | 204/195 X |
| 3,522,162 | 7/1970 | Davies | 204/149 X |
| 3,718,556 | 2/1973 | Rohrback | 204/149 |
| 3,759,816 | 9/1973 | Pretorius et al. | 204/180 G X |
| 3,788,969 | 1/1974 | DiStefano et al. | 204/180 G X |

*Primary Examiner*—Arthur C. Prescott
*Attorney, Agent, or Firm*—S. Michael Bender

[57] ABSTRACT

A light source illuminates particles migrating in an electrophoresis chamber under the influence of a reversing polarity electric field applied between a pair of spaced electrodes which are in the form of thin conductive layers deposited on opposed end portions of the chamber. The light reflected from the particles migrating along the stationary layer of the chamber is imaged onto a circumferentially arranged grating on a transparent rotating disk and modulated thereby. The modulated reflected particle light image is then applied to a photomultiplier tube which in response produces a spectral output signal which is subsequently applied to a frequency translating circuit where it is heterodyned down to the zero frequency region and offset relative to a reference frequency such that the heterodyned signal has a frequency content which is related to mean mobility and a polarity with respect to the offset reference frequency which serves as an indication of the polarity of the charge of the particles migrating in the chamber. A Real Time Analyzer or a frequency tracking circuit may be employed to convert the translator output signal to a mobility histogram or to an accurate measurement of mean mobility, respectively.

15 Claims, 15 Drawing Figures

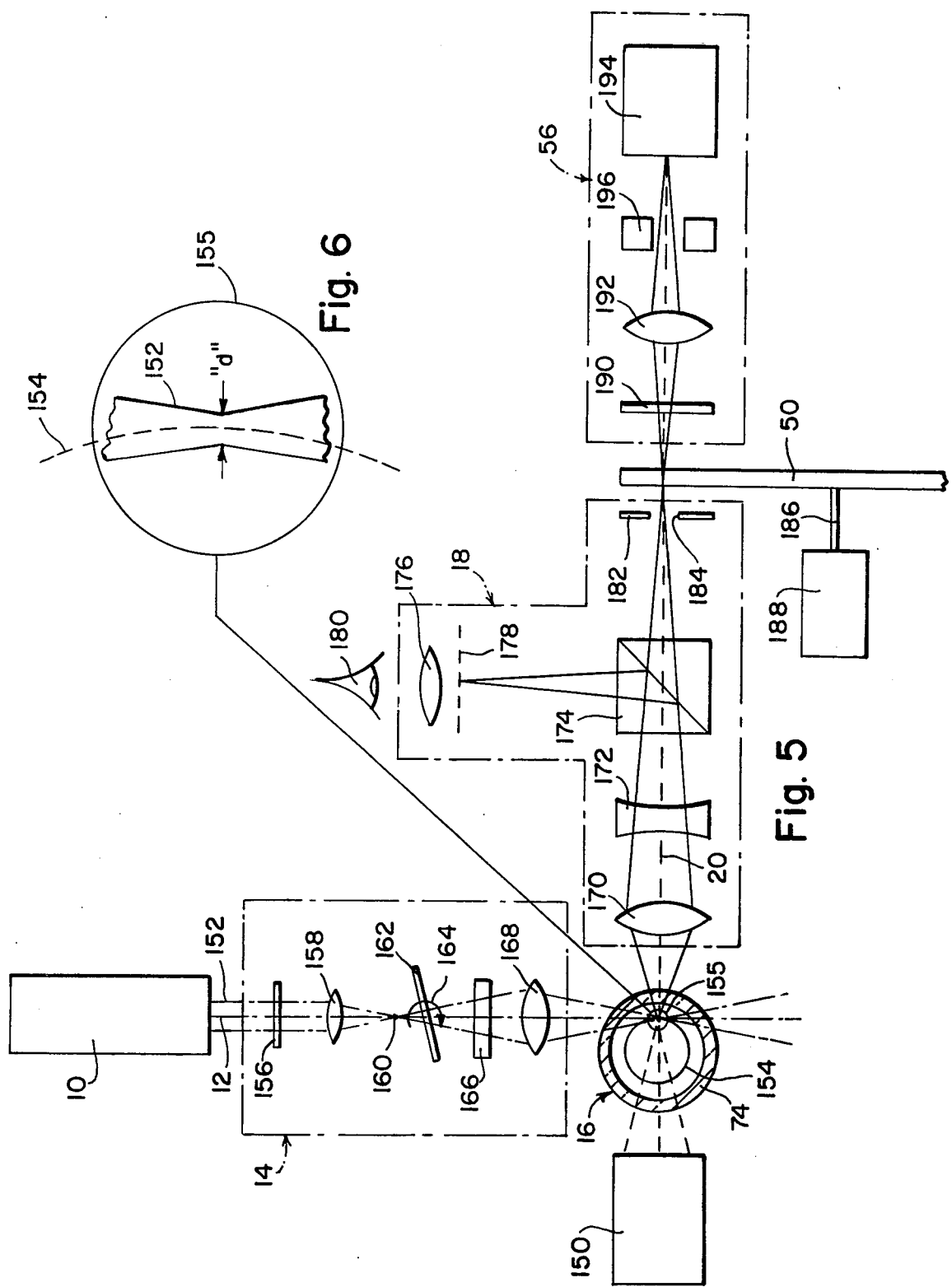

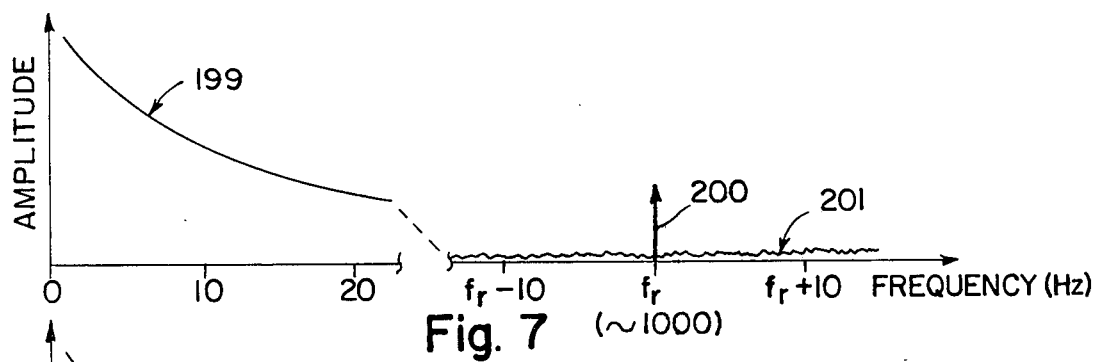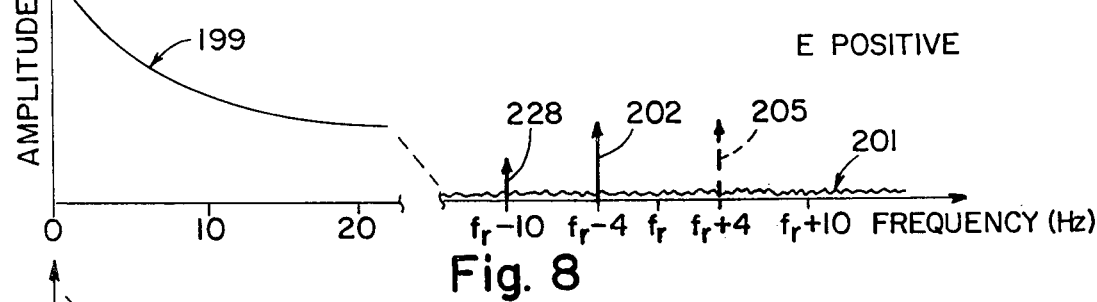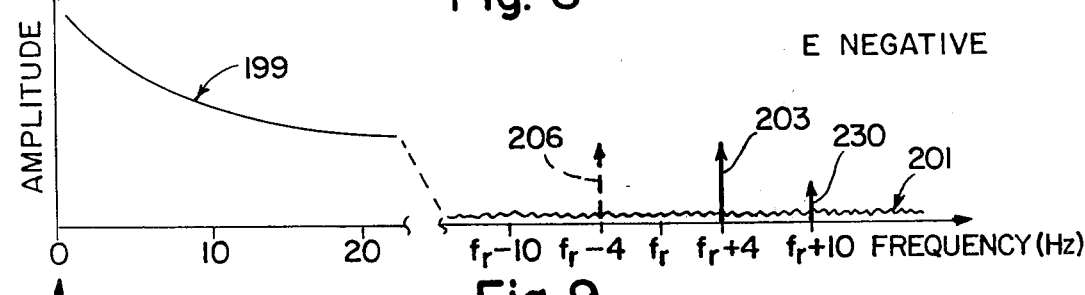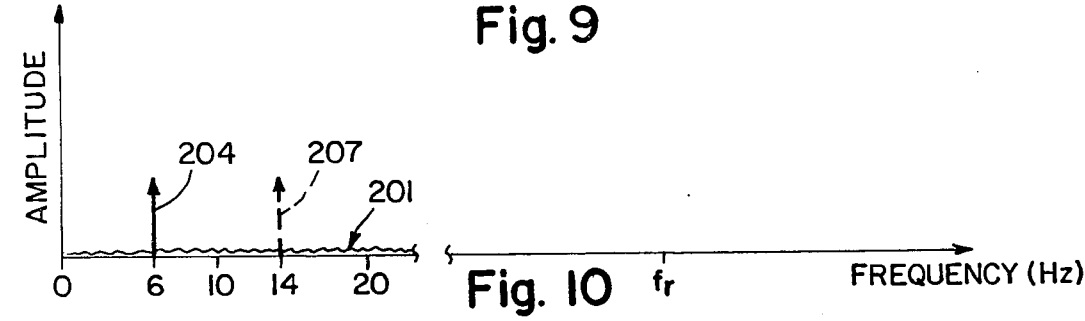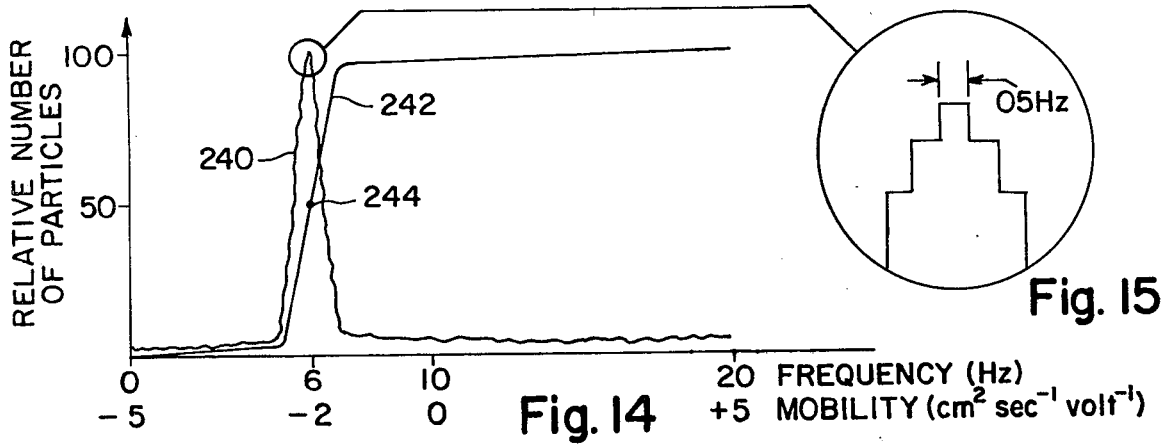

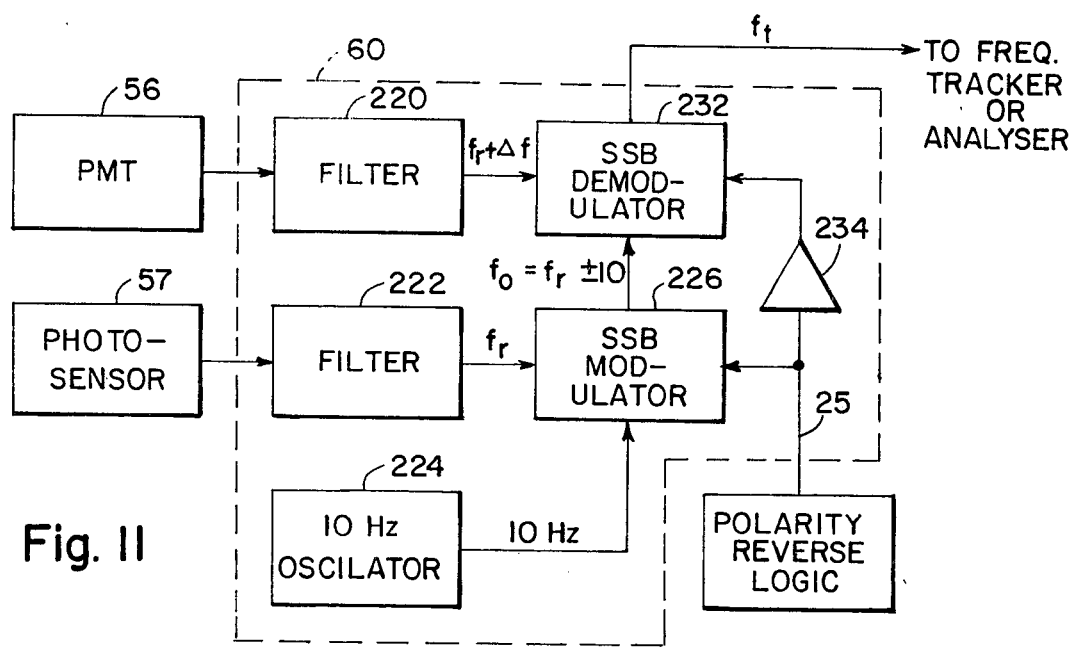
Fig. 11
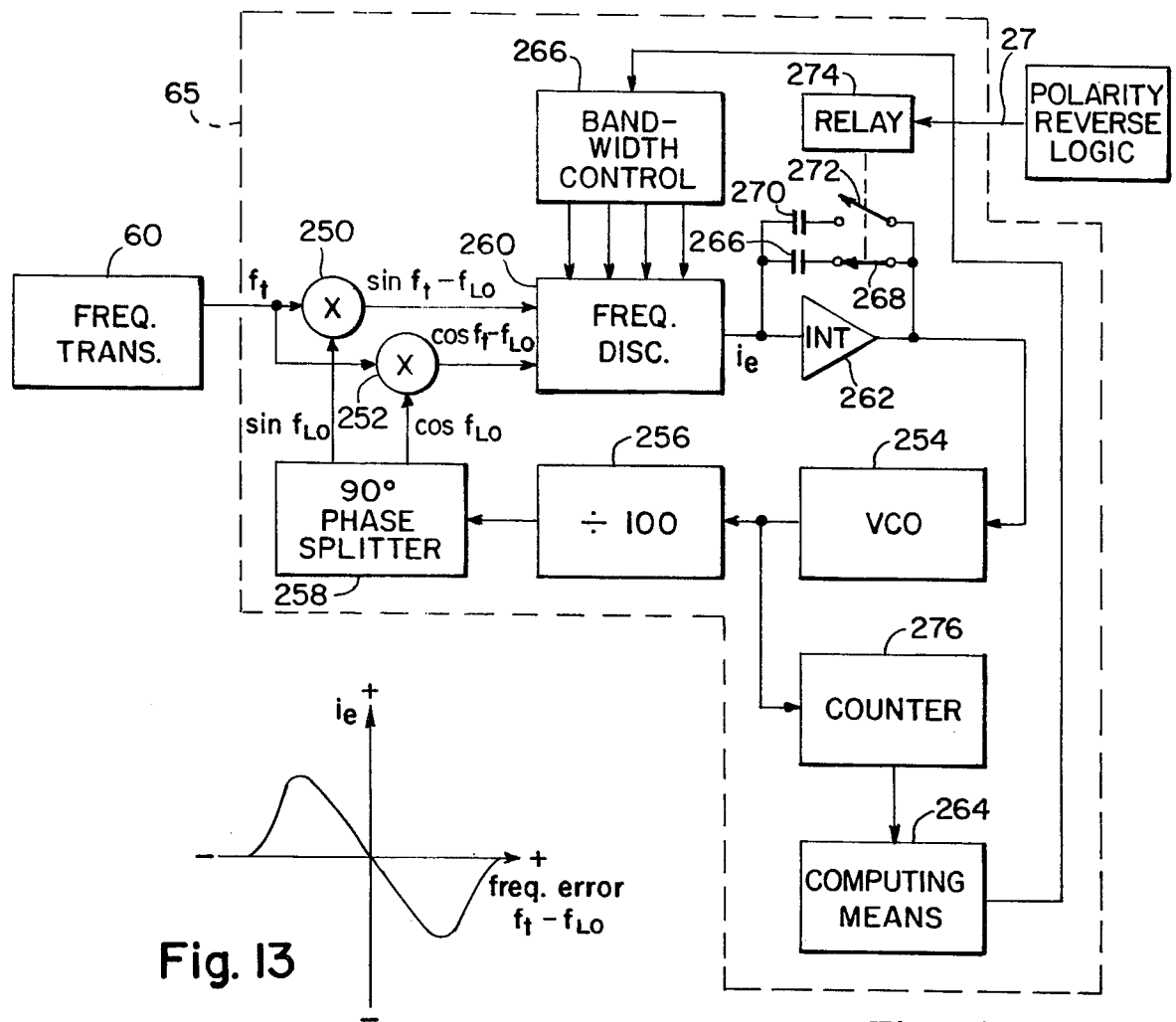
Fig. 13
Fig. 12

AUTOMATIC ELECTROPHORESIS APPARATUS

This is a division of application Ser. No. 767,770 filed Feb. 11, 1977.

The present invention relates generally to apparatus for automatically sensing and/or measuring the electrophoretic mobility or zeta potential of colloidal particles. It is believed that such apparatus is properly classified in Class 204, subclass 209.

As is well known in the art of colloidal chemistry, the term "zeta potential" refers to the net or effective charge on a colloidal particle, usually expressed in millivolts, produced by the interaction of the particle and the medium in which it is suspended. As an example, most natural colloids suspended in an aqueous solution exhibit a net electronegative charge usually within the range of about $-15$ to about $-30$ mv.

Due to this net or effective charge, each charged particle will be caused to migrate within and relative to its bulk suspending medium when an electric field is impressed across a sample of the bulk medium by way of a pair of spaced electrodes, for example. The velocity of each particle per unit electric field strength as expressed in microns/sec per volt/cm is referred to as the electrophoretic mobility of the particle and is designated by the letter u. Zeta potential may be calculated from the known expression:

$$\xi = 36\mu(\eta/\epsilon) \tag{1}$$

where:
$\xi$ = zeta potential (millivolts)
$\mu$ = electrophoretic mobility (microns/sec per volt/cm)
$\eta$ = viscosity (poise)
$\epsilon$ = dielectric constant Since at a given temperature, $\eta$ and $\epsilon$ are constant, expression (1) may be rewritten as:

$$\xi = K_e\mu \tag{2}$$

where $K_e$ equals 14.1 for an aqueous solution (H$_2$O) at 20° C.

Thus, zeta potential may be calculated from the electrophoretic mobility of the particles, which, in turn, is related to the velocity with which the particles pass through the suspending medium under the influence of an applied electrical field.

The classical laboratory or "manual" technique for measuring zeta potential or electrophoretic mobility is exemplified by the patent to Riddick, U.S. Pat. No. 3,454,487, which discloses electrophoresis apparatus comprising an optically clear vessel defining a chamber, a pair of spaced electrodes supported by the vessel for impressing an electric field upon a sample medium in the chamber, a light beam for illuminating the sample medium contained in the chamber, and a microscope for viewing the migration of particles relative to the medium in the chamber when a voltage is impressed across the electrodes. Making measurements of electrophoretic mobility or zeta potential via such apparatus is often referred to as microelectrophoresis whereas the optically clear vessel employed with such apparatus is often referred to as an electrophoreses chamber or cell. In the "manually operated" microelectrophoresis apparatus disclosed in the aforementioned Riddick U.S. Pat. No. 3,454,487, the eyepiece of the microscope includes an ocular micrometer or distance scale and electrophoretic mobility must be measured first by timing the migration or traverse of a single observed particle between gradations on the distance scale with a stop watch, and then employing this information to separately calculate zeta potential from either expressions (1) or (2) above. The manually operated apparatus requires many such repeated operations to accurately determine the zeta potential of the particles in a sample bulk medium and therefore it is time consuming and tedious to employ.

In order to facilitate more rapid and efficient measurements of zeta potential or electrophoretic mobility, attempts have been made to develop a "semi-automatic" microelectrophoresis apparatus as disclosed, for example, in the patent to Greenwood et al, U.S. Pat. No. 3,764,512. In the latter apparatus, a coherent light beam from a laser is caused to intermittently scan a path located on the stationary layer of an electrophoresis chamber by means of a mirror galvanometer at a rate equal to the migration rate of the particles in the chamber. As is well known in this art, the term "stationary layer" refers to an imaginary surface passing through the chamber and which defines the locus of zero velocity with regard to the suspending medium and electro-osmotic phenomena, i.e., when electrophoretic mobility is measured on this surface or stationary layer as it is called, compensation does not have to be made for a velocity component imparted to the suspending medium due to the effects of electro-osmosis. The operator of the "semi-automatic" Greenwood et al apparatus merely views the migrating particles in the chamber through a microscope and simultaneously adjusts the scanning rate of the mirror galvanometer by adjusting a potentiometer in the galvonometer control circuit until the scanning laser beam appears to visually track the migrating particles as viewed through the microscope. Via appropriate scaling circuitry interacting with the galvanometer drive circuit and the circuit supplying the voltage drop across the chamber, a value for zeta potential or electrophoretic mobility may automatically be displayed through suitable means such as an electronically operated digital readout.

In still another form of "semi-automatic" microelectrophoresis instrument fully described in my copending application, Ser. No. 627,299, filed Oct. 30, 1975, and incorporated herein by this reference, means are provided for scanning the light images reflected from the migrating particles rather than scanning the laser illumination beam. That is, a galvanometer driven prism is located internally of the viewing microscope between the microscope objective and the microscope ocular to optically intercept the path of the reflected particle images, and the prism is intermittently scanned in a direction opposite to that of particle migration within the cell. Thus, the operator merely adjusts the galvanometer drive circuit until the apparent motion of the particles as viewed in the eyepiece of the microscope is zero i.e., the particles appear stationary, and the value of zeta potential or electrophoretic mobility corresponding to the particular voltage impressed across the electrophoresis chamber is then instantaneously and automatically displayed.

Although each of the foregoing "semi-automatic" microelectrophoresis instruments represents an improvement over the "manually operable" Riddick type instrument particularly as concerns the speed and efficiency of obtaining zeta potential measurements, there still exists a need for a fully-automatic electrophoresis apparatus that is for all intents and purposes totally independent of operator involvement. Such an "automatic" apparatus purportedly is disclosed for example, in Flower et al, No. 3,793,180 and includes a fixed reticle or ruled grating upon which laser light reflected from migrating particles in an electrophoresis chamber is directly imaged by a microscope. The reflected migrating particle images are modulated by the ruled grating and the modulated signal applied to the photocathode surface of a photo-multiplier tube. The output signal of the photo-multiplier may then be processed to yield information related to the electrophoretic mobility and thusly, the zeta potential of the particles in the chamber. In the Flower et al automatic apparatus however, the nature of the useful output information obtainable is limited by the fact that the laser light reflected particle image is modulated by a fixed reticle or grating; and furthermore, the apparatus lacks the ability to process many different types of colloids or suspended particles automatically in a rapid and continuous manner. In addition, this patent does not teach how to operate the apparatus disclosed therein in conjunction with an electric field applied across the electrodes in the chamber which reverses its polarity periodically, and therefore, any measurements made by the system disclosed therein are susceptible to relatively large errors.

Against the foregoing background, it is the objective of the present invention to provide an improved automatic electrophoresis apparatus.

Toward the accomplishment of this and additional objectives and advantages, he present invention, briefly summarized, comprises a light source for illuminating particles migrating in an electrophoresis chamber under the influence of a reversing polarity electric field applied between a pair of spaced electrodes which are in the form of thin conductive layers deposited on opposed end portions of the chamber. The light reflected from the particles migrating along the stationary layer of the chamber is imaged onto a circumferentially arranged grating on a transparent rotating disk and modulated thereby. The modulated reflected particle light image is then applied to a photomultiplier tube which in response produces a spectral output signal which is subsequently applied to a frequency translating circuit where it is heterodyned down to the zero frequency region and offset relative to a reference frequency such that the heterodyned signal has a frequency content which is related to mean mobility and a polarity with respect to the offset reference frequency which serves as an indication of the polarity of the charge of the particles migrating in the chamber. A Real Time Analyzer or a frequency tracking circuit may be employed to convert the translator output signal to a mobility histogram or to an accurate measurement of mean mobility, respectively.

The foregoing and still other features and advantages as well as a more complete understanding of the present invention will be made apparent from a study of the following detailed description of preferred embodiments of the invention in connection with the accompanying drawings wherein:

FIG. 5 is a schematic diagram of the electrophoresis apparatus of the present invention showing the optical components thereof;

FIG. 6 is an enlarged cross-sectional view of a portion of the electrophoresis chamber of FIG. 5;

FIGS. 7–10 are schematic representations in the frequency domain depicting the signal translation accomplished by the circuit of FIG. 11;

FIG. 11 is a schematic block diagram of the signal translation circuit according to the present invention;

FIG. 12 is a schematic block diagram of the frequency tracker circuit according to the present invention;

FIG. 13 is a graphical depiction of the characteristic of the frequency discriminator of the circuit of FIG. 12;

FIG. 14 is a facsimile of a mobility histogram obtainable from the apparatus of the present invention; and FIG. 15 is an enlarged depiction of a portion of histogram representation of FIG. 14.

With reference to the foregoing drawings, the preferred embodiments of the present invention will now be described in detail.

GENERAL ORGANIZATION

Figure 1:
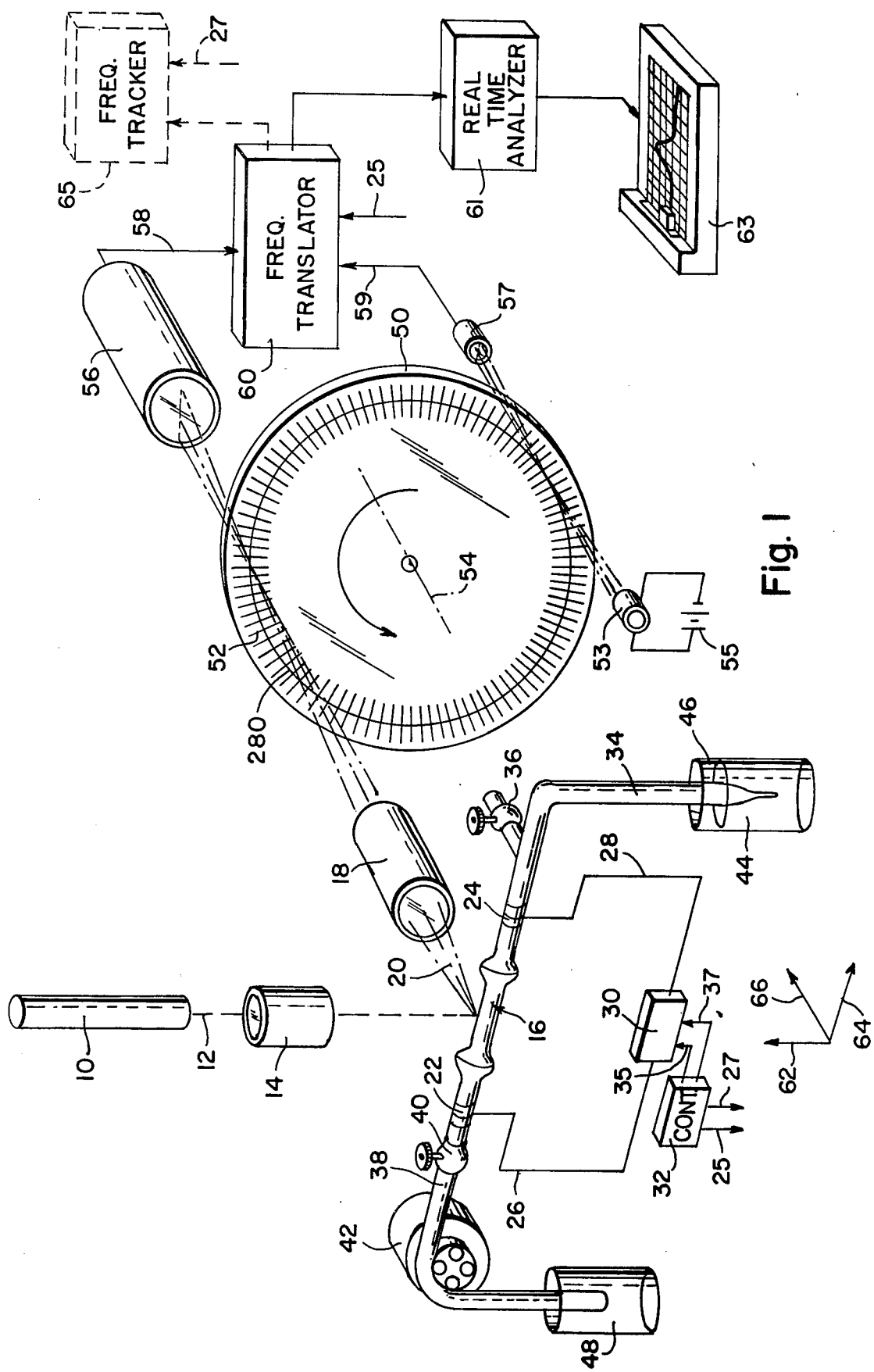
FIG. 1 is a schematic representation of the basic components of the electrophoresis apparatus of the present invention.

As depicted in FIG. 1, an illumination source in the form of a laser 10 directs a well collimated generally cylindrically shaped beam of coherent light along optical path 12 to the input side of beam shaping module 14. The laser light beam emerges from beam shaping module 14 along optical axis 12 with its transverse cross-sectional shape altered in such a manner as to efficiently illuminate a region interiorly of tubular electrophoresis chamber 16 approximately complementary to the depth of field and field of focus of microscope 18 which latter is suitably situated so as to view the illuminated region interiorly of chamber 16 along optical axis 20.

Tubular electrophoresis chamber 16 has a pair of electrodes 22, 24 at opposed ends thereof which are connected via conductors 26, 28 to a conventional constant current source (D.C.) indicated generally at 30. A suitable controller 32 is provided which feeds a pair of output signals to the current source 30 on lines 35 and 37 respectively, for controlling the magnitude of the current supplied by source 30 and the polarity of the current, respectively. For purposes of understanding the present invention, it will be sufficient to note that if line 37 contains no signal the polarity of the current provided by source 30 is such as to apply a positive electric field across electrodes 22, 24 in chamber 16. If line 37 contains a signal, the polarity is reversed and the electric field across the electrodes will be negative. These signals referred to hereinafter as Polarity Reverse Logic signals are made available for use elsewhere in the apparatus on lines 25, 27. The rate of polarity reversal is thus directly proportional to the rate at which the Polarity Reverse Logic signals appear on lines 37, 25 and 27 and this rate may be selected and/or changed via controller 32. The purpose of such logic signals will be made more apparent below. At present, suffice it to note that as a result of the action of the controller 32 and the constant current source 30, an electric field of preselectable magnitude whose polarity is reversed at a preselectable rate may be impressed across electrodes 22 and 24.

A tubular input line 34 is connected through a valve-operated T-connection 36 to the end of chamber 16 corresponding to electrode 24 whereas a tubular output line 38 is connected through a valve 40 to suitable pump means such as a conventional peristaltic pump indicated generally by reference numeral 42. A sample colloidal dispersion 44 in container 46 may be drawn into chamber 16 to fill the chamber portion extending between electrodes 22 and 24 via input line 34 and suitable operation of valve 40 and peristaltic pump 42 with any waste dispersion being collected in container 48.

The altered laser light beam emitted by beam shaping module 14 along optical axis 12 impinges upon the dispersed colloidal particles in chamber 16. Reflected particle light images are viewed by microscope 18 along optical axis 20 and are directed by the microscope along this optical axis to and through the outer circumferential periphery of transparent rotating disk 50. The disk 50 has a series of circumferentially arranged evenly spaced, opaque lines 52 to form a grating extending completely circumferentially about the periphery of the disk substantially as shown, and has its rotation axis 54 aligned parallel to optical axis 20 such that when disk 50 rotates about axis 54, the grating of opaque lines 52 will intercept the reflected particle light images thereby modulating them as a function of the spacing between the lines of the grating and the angular velocity of the disk. The modulated reflected particle light images are then applied to a sensing device in the form of a photomultiplier module 56 aligned along optical axis 20 to produce on output line 58 a spectral signal related to the modulated light image. This spectral output signal is then applied to a frequency translator circuit indicated generally by block 60.

An auxiliary source of constant illumination, such as a light-emitting diode 53, powered by voltage supply 55 also directs a beam of light through the rotating grating of disk 50 which beam of light is also modulated thereby. This auxiliary modulated light beam signal is then applied to a photosensor 57 which produces on output line 59 an output signal which serves as a reference signal related to the exact rotational speed of the disk 50. For purposes which will be more fully explained, the disk rotation speed reference signal and the Polarity Reverse Logic signals from controller 32 are applied as inputs via lines 59 and 25, respectively, to frequency translator circuit 60.

In the absence of any current passing between the electrodes 22, 24 in chamber 16, the particle velocity in the chamber will essentially be zero except for relatively minor velocity components due to Brownian motion. Under this condition, the translator circuit 60 output signal will exhibit a primary frequency component related to the rotation frequency of the disk and will have a magnitude related to the number of particles in the chamber viewed by microscope 18. However, should a current be passed between electrodes 22, 24 as by operation of controller 32 and constant current source 30, the particles will migrate in the chamber in a direction parallel to the central longitudinal axis of the chamber due to electrophoretic phenomena, and as a result, the reflected particle light images being modulated by the rotating grating on disk 50 will exhibit an additional velocity component circumferentially with respect to the grating. This will shift the frequency of the photomultiplier output signal up or down depending upon the direction of the additional velocity component. The translator circuit then automatically produces an output signal the frequency of which is related to the electrophoretic mobility of the particles in the chamber 16. When the translator output signal is applied to a Real Time Analyser indicated generally by reference numeral 61 the latter produces a useful histogram of the charge or mobility distribution of the particles in the chamber 16 which, in turn, may be recorded by a conventional chart recorder 63. Alternatively, the translator output signal may be applied to a frequency tracking circuit 65 which has the capability of measuring the mean mobility of the particles migrating in chamber 16 under the influence of the applied electric field.

It will be appreciated with respect to the general organization of the invention as diagramatically indicated in FIG. 1, that the electrophoretic velocity component is measured along an axis parallel to the central longitudinal axis of the electrophoresis chamber, that this axis of measurement is mutually perpendicular to both the optical axis 12 and the optical axis 20, and that the electrophoretic velocity component measurement axis, the optical axis 12, and the optical axis 20 mutually intersect at a point on the stationary layer of the chamber. Thus, as indicated in FIG. 1, a particle migrating along the stationary layer of chamber 16 has its electrophoretic velocity vector parallel to arrow 64, is illuminated by laser 10 along an optical path parallel to arrow 62, and the image of this migrating particle is viewed by microscope 18 along an optical path parallel to arrow 66.

THE ELECTROPHORESIS CHAMBER

Figure 2:
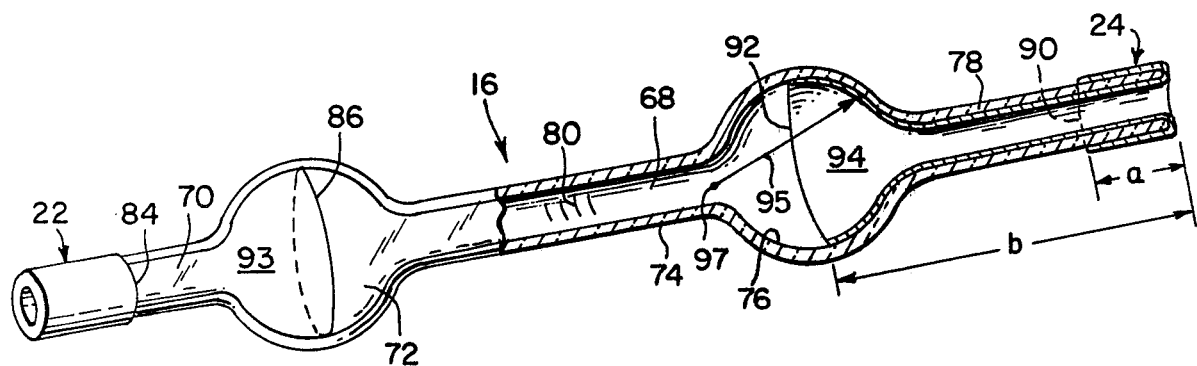
FIG. 2 is a perspective view partially broken away, of the electrophoresis chamber of the present invention.

Turning now to FIG. 2, electrophoresis chamber 16 in its preferred form generally comprises a hollow tubular member having a central bore 68 extending commonly through a first cylindrical end portion 70, a first globular portion 72, a central cylindrical portion 74, a second globular portion 76 and a second cylindrical end portion 78. The chamber is fabricated from an optically transparent, dimensionally stable, non-reactive substance such as quartz and is vacuum formed on a cylindrically shaped mandrel in a known manner, the mandrel having a precisely dimensioned outside diameter. The first globular portion 72 and second globular portion 76 are formed by locally heating the quartz tube after it has been removed from the mandrel while spinning the tube in a glass lathe. As shown in FIG. 2, the central cylindrical portion 74 of the chamber 16 has engraved on its interior surface a plurality of circumferentially extending lines evenly spaced approximately 250 microns apart. These lines which are employed for calibration purposes in a manner to be more fully described below, may be formed as by engraving the precision mandrel thus transferring the lines to the interior surface of the vacuum formed quartz tube. In the preferred embodiment described herein, the electrophoresis chamber 16 has a length of 80 mm, an inner diameter of 1 mm, a wall of thickness of 0.5 mm, and the first globular and second globular portions 72, 76 have a nominal inside diameter of 3 mm; however, these dimensions are not critical and may be varied to suit particular requirements.

A first electrode 22 in the form of a thin continuous film or layer of platinum extends from a first terminating circumferential boundary 84 on the exterior surface of first cylindrical portion 70 toward and around the cylindrical tubular extremity of the first portion whereupon the platinum electrode layer extends inwardly and axially with respect to through bore 68 along the interior surface of the first cylindrical portion thence into the first globular portion terminating at circumferential boundary 86. The continuous electrode layer 22 thus includes coaxial inner and outer portions with the axially terminal part of the inner portion affording a substantially hemispherical shape coextensive with the left-most portion of first globular portion 72. Likewise, there is provided a second electrode 24 in the form of a thin continuous film or layer of platinum extending from a first terminating circumferential boundary 90 on the exterior surface of second cylindrical portion 78 toward and around the cylindrical tubular extremity of the second portion whereupon the platinum electrode layer extends inwardly and axially with respect to through bore 68 along the interior surface of the second cylindrical portion into the second globular portion and terminates at circumferential boundary 92. The continuous electrode layer 24 thus also includes coaxial inner and outer portions with the axially terminal part of the inner portion affording a substantially hemispherical shape coextensive with the right-most portion of second globular portion 76. Thus, there is disposed interiorly on the surface of tubular chamber 16 a pair of spaced, opposed substantially hemispherically shaped electrode surface portions 93, 94 at either end respectively of the central cylindrical portion 74 of the chamber, with surface portions 93, 94 being in electrical circuit continuity with the outer portions of electrodes 22, 24 located on the exterior surface of first cylindrical end portion 70 and second cylindrical end portion 78, respectively. By this arrangement, conductors 26, 28 (FIG. 1) may suitably be electrically connected to the outer portions of electrodes 22, 24 for passing an electric current from source 30 between the spaced substantially hemispherically shaped electrode surface portions 93, 94 and axially through the central cylindrical portion 74 of the chamber 16.

In prior art electrophoresis apparatus, the formation of gas bubbles due to electrolysis of the medium within the chamber usually can be avoided by employing a relatively large electrode surface. In the present invention, however, the electrophoresis chamber and the electrode surfaces are relatively small and therefore, despite high current densities such electrolysis is avoided in a novel manner, namely, by the use of substantially hemispherically shaped electrode surfaces as already described. It has been discovered that substantially uniform current distribution across the electrode surfaces of the present invention may be achieved by having the actual shape of each substantially hemispherical electrode surface defined by an imaginery spherical surface having a radius of curvature 95 and a center of curvature 97 which center is for each electrode surface located at the intersection of the central axis of central tubular portion 74 and a transverse plane passing through chamber 16 at the juncture of the central tubular portion and a corresponding one of the first and second globular portions 72 and 76. Thus, it will be appreciated that globular portions 72, 76 are not strictly speaking, spherical in shape, and that the respective portions of each globular portion 72, 76 coextensive with each electrode surface exhibit a curvature that is less than that of their corresponding remaining portions not coextensive with an electrode surface. By this construction, an electrode surface may be formed which is equidistant throughout its extent relative to point 97 at each end of the central tubular portion, respectively which, in turn, produces a uniform current distribution across each electrode surface thus tending to prevent electrolysis and consequent displacement of the suspending fluid thereby preventing an error in the measured electrophoretic velocity.

In situations where relatively low ionic strength sample dispersions are being measured, say, less than 10 $\mu$mhos/cm, for example, satisfactory results may be achieved by a slightly modified alternatively preferred chamber construction (not shown) wherein the globular portions 72, 76 are omitted and chamber 16 is in the form of a tubular cylindrical member. That is, in the alternative preferred form of electrophoresis chamber, the entire chamber 16 is in the form of a hollow cylindrical tube and the inner portions of the electrode layers have axial terminal parts coextensive with the cylindrical bore of the tube i.e., they are cylindrically shaped rather than substantially hemispherically shaped, the former being employed to measure sample dispersions of relatively low ionic strength whereas the latter is recommended for use in measuring the zeta potential or mobility of sample dispersions having a relatively high ionic strength. It will be appreciated, therefore, that in its broadest sense, the novel electrophoresis chamber construction of the present invention calls for a tubular member having a pair of spaced electrodes at least one of which is in the form of a thin electrically conductive film or layer deposited on an end portion of the tubular member in such a manner as to have both an outer portion and an inner portion electrically connected to each other and being in at least a partial overlapping or coaxial disposition relative to each other.

In accordance with the present invention, the preferred electrode material comprises a first layer of platinum and a second layer of palladium, although for dispersions having a conductivity less than about 1000 $\mu$mhos/cm the layer of platinum will suffice. As already alluded to, under certain conditions due to electrolysis, it is common to evolve hydrogen gas at the cathode and oxygen gas at the anode when a current is passed through a sample dispersion in an electrophoresis chamber. Such gassing in the vicinity of the electrodes produces small bubbles which lead to errors in the measured electrophoretic velocity component and thus, are extremely undesirable. By employing a palladium electrode surface in accordance with the present invention, it has been found that the palladium has the capacity as a cathodic element to absorb relatively large amounts of free hydrogen into its lattice structure, thus preventing the hydrogen gas from being evolved in the form of bubbles which would result in an error producing displacement of the dispersion or fluid sample in the chamber 16. Subsequently, the charged palladium electrode can function as a non-gassing anode until the hydrogen charge is depleted. This is highly advantageous in electrophoresis apparatus such as the present invention where an electric field of reversing polarity is applied between the electrode surfaces and each electrode surface alternatively functions as a cathode and as an anode.

In order to deposit the platinum/palladium electrode layer on the surface of the tubular quartz member, the latter is held in a vertical position and dipped into a platinum-organic compound such as is made available by Engelhard Industries under the trademark Liquid Bright Platinum Model 05X. The tube is dipped into the platinum compound a distance indicated by the letter "a" in FIG. 2, and a quantity of the compound is drawn by vacuum up through the interior or bore of the tube a distance indicated by the letter "b". The tube is then drained by gravity and centrifuged to remove excess compound leaving a continuous uniform layer on the inner and outer surface of the tube. The tube is next fired at about 600° C. in a furnace to drive off the organic component and permanently bond the platinum layer to the surface of the tubular member. The process is then repeated to form a similar platinum layer bonded to the other end of the tube/chamber.

This first platinum layer although permanently bonded to its quartz undersurface is too thin to serve as an electrode and in fact, merely serves as an intermediate layer or bonding layer between the quartz surface and either an additional layer of platinyzed platinum, or an additional layer of palladium. Thus, the bonding layer is either platinyzed to receive an additional layer of platinum; or a layer of palladium is electrolytically deposited on the bonding layer.

It has been found satisfactory to merely deposit the palladium top layer in the region of the hemispherically shaped terminal inner axial part of each electrode surface to effect complete reduction of gassing at the electrodes. For example, a 10 mg. quantity of palladium electrolytically deposited on the hemispherical portion of the electrode surface, is capable of providing 8 amp. seconds of charge before the hydrogen saturates the electrode and finally evolves gas. Once charged with hydrogen, the palladium coated electrode is then capable of functioning as a non-gassing anode, combining with oxygen and forming water until the hydrogen charge is exhausted.

After the electrodes 22, 24 are formed on the tubular quartz body or chamber 16 as aforesaid, the latter is cleaned preferably by exposure to ultrasonic vibrations, for example, and then is coated inside and out with a thin layer of silicone such as that supplied by Peerless chemical under the trademark SC-87. Since the silicone layer is non-wetting, it aids in keeping the chamber 16 clean and furthermore, has been found to significantly reduce the inherent charge on the surface of the tubular quartz body thereby correspondingly reducing the magnitude of the electroosmotic effect between the chamber and any sample dispersion in the central cylindrical portion thereof. And although the silicone which normally is a good insulator, will also be applied as a thin coating to the surface of the electrodes 22, 24, the silicone will not adversely effect the electrical operation of the electrodes providing it is not applied in excess, rather it will serve to protect the electrode surfaces and aid in maintaining them in a clean condition.

Figure 3:
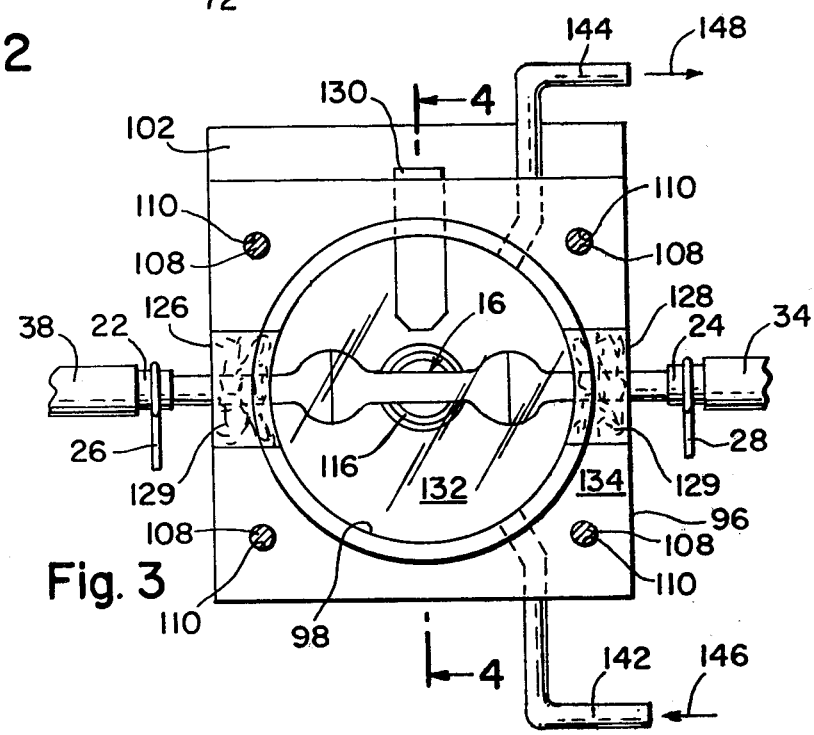
FIG. 3 is a front elevational view of the electrophoresis chamber of FIG. 2 mounted in a water-bath fixture according to the present invention.
Figure 4:
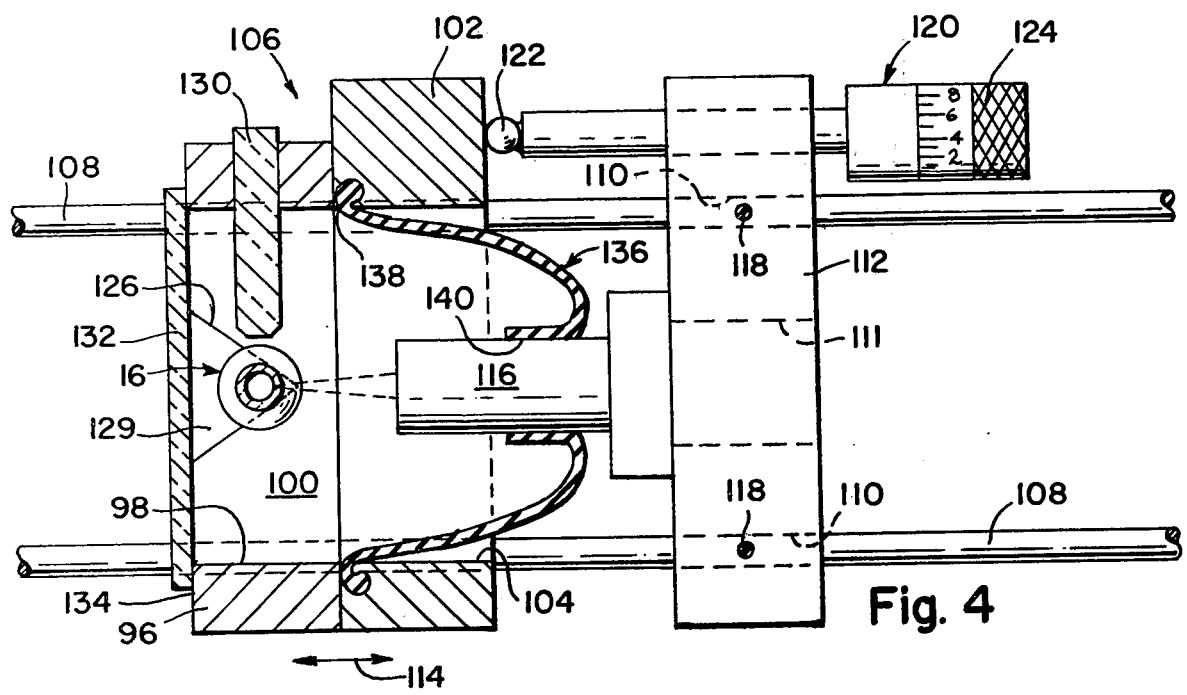
FIG. 4 is a side elevational view partly in section of the fixture of FIG. 3 and of the microscope objective mounted in an adjacent fixture shown slightly enlarged with respect to FIG. 3.

As described above in connection with FIG. 1, the electrophoresis chamber 16 is mounted relative to laser light source 10 and beam shaping module 14 on the one hand, and microscope 18 and rotating disk 50 on the other hand. Turning now to FIGS. 3 and 4, the preferred manner in which the completed electrophoresis chamber 16 is mounted relative to these other parts will now be described. As substantially shown, electrophoresis chamber 16 is mounted for support in a frame member 96 having a central cylindrical bore 98 defining the first portion of a water-bath cavity 100. A second frame member 102 is rigidly affixed to first frame member 96 by a plurality of threaded fasteners (not shown) and includes a similar central cylindrical bore 104 defining the second portion of the water-bath cavity 100.

Frames 96, 102 comprise a unitary carriage assembly generally indicated by reference numeral 106 which, in turn, is supported on a plurality of cylindrical rods or rails 108 by means of a like plurality of cylndrical opening 110 passing completely through carriage assembly 106 as depicted. The openings 110 are suitably sized relative to rails 108 so that the carriage assembly 106 is freely movable relative to rails 108 and to a third frame member 112 in a horizontal back and forth direction as indicated by arrow 114 (FIG. 4). Third frame member 112 also is supported on rails 108 via a plurality of openings 110 and fixidly carries thereon the objective lens housing 116 of microscope 18 (FIG. 1). The frame member 112 includes a central opening to provide an optical path between the objective lens inside its housing 116 and other optical components of the microscope 18 as will be described in more detail below.

While third frame member 112 is also freely movable on rails 108 in the same manner as carriage assembly 116, the third frame member 112 includes a plurality of conventional set screws 118 which extend into the frame member 112 and which may selectively be tightened down in abutting engagement against the rails 108 thereby affixing the third frame members 112 in a stationary position relative to the rails 108. Also supportingly affixed to the third frame member 112 is a micrometer 120 whose spindle 122 is in abutting engagement with the carriage assembly 106 as shown in FIG. 4. Thus, rotation of the micrometer barrel 124 will effect precise movement of carriage assembly 106 relative to objective lens 116 in the direction of arrows 114. A conventional spring assembly is positioned relative to the carriage assembly 106 and the third frame member 112 to maintain the carriage assembly resiliently biased against the micrometer spindle 122 and thus assure that the carriage assembly movement will always follow that of the spindle; however, the spring assembly has not been shown to avoid confusing the drawings.

As shown, electrophoresis chamber 16 is fixedly mounted in a horizontal position in frame member 96 transversely of cylindrical bore 98 and the water-bath cavity 100. In order to precisely position the chamber 16 in its desired horizontal position, the first cylindrical end portion 70 and second cylindrical end portion 78 of the chamber are received in a corresponding pair of precision V-blocks 126, 128 carried in each opposite side of the first frame member 96. The V-blocks are dimensioned such that when the chamber 16 is seated therein the axis of the central cylindrical portion 74 of the chamber will commonly intersect the optical axis of the microscope objective lens 116. In order to provide an optical path for the laser light beam being directed along axis 12 a light transmissive plug 130 is vertically mounted in the first frame member 96 substantially as shown.

After the chamber 16 has been properly positioned in the V-blocks 126, 128 a water-tight sealing or potting compound is applied to V-blocks as at 129 to maintain the chamber in position and provide a water-tight seal at the sides of the frame member 96 with regard to the water-bath cavity 100.

The first portion of the water-bath cavity 100 is further sealed by a glass plate 132 cemented or otherwise affixed in a water-tight manner to face 134 of first frame member 96 whereas the second portion of the water-bath cavity is sealed by means of a water-tight flexible cylindrical diaphragm or bellows 136 having one end 138 suitably fastened in a water-tight manner between frame members 96 and 102, and having its other end 140 suitably fastened in a water-tight manner around objective lens housing 116 which latter extends into the water-bath cavity 100 through latter's second portion i.e., bore 104, frame 102. An inlet tube 142 is provided in frame member 96 communicating between the exterior of the frame member and the water-bath cavity 100 while an outlet tube 144 is also provided for communicating between the interior of the water-bath cavity and the exterior of the frame member 96. As indicated by arrows 146, 148, FIG. 3, a constant temperature medium such as thermostatically controlled, water or other fluid, for example, is caused to flow via inlet tube 142 into the water-bath cavity 100 and exit via outlet tube 144 thus maintaining the sample dispersion located in the central cylindrical portion of the electrophoresis chamber at a constant temperature. Owing to the flexible nature of the water-tight bellows member 136, the carriage assembly 106 may be moved relative to the objective lens housing 116 via the selective actuation of micrometer 120 to effect focusing of microscope 18 on the stationary layer of chamber 16 without disturbing the integrity of the constant temperature water-bath which always envelops at least the central cylindrical portion of the chamber and preferably envelops the globular cavities containing the electrode surfaces 93, 94 as well. Micrometer 120 has a range of adjustment sufficiently large enough to enable movement of carriage assemby 106 relative to third frame member 112 and objective lens housing 116 of microscope 18 so as to permit focusing of the microscope objective on the back inside surface of the central cylindrical portion 74 of the chamber, on the front inside surface thereof, or any point therebetween with the depth of the field of focusing extending in the direction of arrows 114.

The foregoing description of the preferred manner of mounting the electrophoresis chamber 16 relative to the objective lens 116 of microscope 18 was given in considerable detail because the chamber mounting means also serves the dual function of providing a constant temperature water-bath means for the chamber thus constituting an important feature of the present invention. It will be understood that the other components of the automatic electrophoresis apparatus of the present invention may suitably be mounted relative to the chamber 16 by employing frames and rails similar to frame 112 and rails 110, however, since the details of the mounting means for these other components form no part of the present invention they will be omitted for the sake of brevity. Suffice it to say, any well known mounting hardware may be employed to arrange these components relative to the other parts as described herein as will occurr to those of ordinary skill in the art.

CHAMBER ILLUMINATION OPTICS

Turning now to FIG. 5 which is similar to FIG. 1, but schematically shows the optical components of the apparatus of the invention in somewhat greater detail, a conventional brightfield illumination source indicated generally by reference numeral 150 is shown illuminating the central cylindrical portion 74 of chamber 16 from a side of the chamber oppositely disposed relative to microscope 18 and its objective lens 116. The chamber is shown in cross-section and its size is greatly exaggerated relative to the schematic representations of other parts to aid in understanding the principles of the invention. Because the contrast afforded by a brightfield illumination system is inadequate to illuminate small-sized colloidal particles i.e., particles smaller than 0.2 μm, the bright-field illuminator 50 is employed primarily for setting-up and calibrating the apparatus as will be explained in greater detail below. For illuminating the chamber during normal operation when the zeta potential or electrophoretic mobility of a sample dispersion is being measured, a dark-field illumination system is employed comprising the laser light source 10 and beam shaping module 14 (see also FIG. 1). The laser light source which may comprise a Hughes Model 3222H-PC 2 mW polarized helium neon laser, directs a well collimated beam of light 152 of substantially circular cross-section along optical axis 12 through the beam shaping module 14 and is ultimately focused in the region of the stationary layer 154 of the chamber 16. As well known in the art, the stationary layer in a tubular or cylindrically shaped electrophoresis chamber is an imaginery cylindrical surface spaced a distance 0.707R from the central longitudinal axis of the chamber where R is the radius of the chamber. Thus, the stationary layer is indicated in FIG. 5 by the circle 154. The function of beam shaping module 14 is to reshape the circular laser beam 152 into a vertical curtain of laser light which in the vicinity of the stationary layer 154 in chamber 16 converges to a thickness or depth "d" as shown in FIG. 6, the latter being a greatly enlarged schematic representation of a portion of the circle 155 of FIG. 5. The thickness "d" is chosen to be approximately the same as the depth of field of focus of the microscope objective 116 and is approximately 10μ in the preferred embodiment.

In order to accomplish the foregoing, the beam shaping module comprises a half-wave retardation plate 156 for rotating the plane of polarization of the laser beam 152; a convex lens 158 which may be a 40× microscope objective for focusing the beam 152 at a point 160; a thin glass late 162 which may be selectively angularly varied as indicated by arrow 164 to adjust the lateral position of beam 152 relative to the stationary layer 154 in chamber 16; a cylindrical lens 166 to spread the beam in a direction perpendicular to the plane of the drawing, and finally, a second convex lens 168 to focus the reshaped beam at the point where it intercepts the optical axis 20 of microscope 18. In the preferred embodiment, the reshaped beam has width (i.e., its transverse dimension perpendicular to the plane of FIGS. 5 and 6) of approximately 1 mm and is approximately equal to the width of the field of view of microscope objective lens 170 supported inside housing 116 (FIG. 4). In this manner, the reshaped laser beam illuminates only particles in the chamber central cylindrical portion which are in focus and within the field of view of the microscope 18.

MICROSCOPE OPTICAL SYSTEM

As described above in connection with FIGS. 3 and 4, the objective lens 170 inside its housing 116 is immersed in the water-bath of cavity 100 and is supported on the frame member 112 which, in turn, is mounted on a plurality of rails 108. As schematically shown in FIG. 5, the remaining components of the microscope 18 all of which may also be supported on similar frame members mounted on rails 108 comprise a negative focal length cylindrical lens 172 which serves as an astigmatism compensator; a conventional beam splitting prism 174 for transferring the image viewed by objective lens 170 to an eyepiece lens 176 having a reticle 178 and through which an observer at 180 may view the microscope image; and finally, a diaphragm 182 having a slit 184 for controlling and limiting the image being focused on the disk 50 (FIG. 1).

To appreciate the desirability of the astigmatism compensation lens 172, assume that the electrophoresis chamber 16 is filled with a colloid convenient for calibration and alignment procedures such as a dilute aqueous suspension of spherical $0.1\mu$ diameter latex particles. Assume further that the microscope objective 170 is focused at the front stationary layer i.e. within circle 155, and that the curtain of laser illumination 152 has also been positioned to coincide with this stationary layer by suitable angular rotation of the glass plate 162. Since the particles are smaller than the wavelength of the laser illumination, the microscope cannot resolve their shape. Rather, the image an observer at 180 sees through the microscope eyepiece 176 corresponds to the diffraction pattern of the overall microscope system. If the system were optically perfect, the diffraction pattern would correspond to the familiar "airy disk" which would contain approximately 85% of the total power and one or more concentric rings containing the rest of the illumination. Unavoidably, the finite thickness of the curved walls of the central cylindrical portion 74 of the electrophoresis chamber causes an astigmatism of the viewed image. In viewing a submicron sized particle, the effect of this astigmatism is to produce a more complicated and larger diffraction pattern. If larger particles, in the $2-20\mu$ range, are viewed using the conventional bright-field microscope illuminator 150, the astigmatism would manifest itself simply as a loss of sharpness and contrast. In accordance with the present invention, however, the astigmatism, in either case, is eliminated by means of the negative focal length cylindrical lens located at a precise pre-determined distance from the focal plane of eyepiece lens 176. The purpose of cylindrical lens 172 is to produce an astigmatism which is exactly opposite to, and in the same axis as, the astigmatism produced by the curved walls of the chamber 16. The precise position and focal length of such lens is dependent upon the thickness of the walls of the electrophoresis chamber. Typically, a wall thickness of 0.5 mm requires a cylindrical lens having a focal length of approximately 1200 mm spaced approximately 140 mm from the eyepiece lens focal plane. The precise position of the cylindrical lens is readily determined by moving the lens in its frame member laterally along rails 108 until the best diffraction pattern is seen through the eyepiece lens 176.

An alternative method of astigmatism correction may be employed which utilizes a positive lens of approximately the same power as the cylindrical lens 172 but oriented at right angles with respect to the cylindrical lens 172. It functions to introduce an astigmatism of the same magnitude and sign in one axis as the walls of the chamber cause in the other axis. The disadvantage of this method results from the fact that changes in the astigmatism correction produce magnification changes along the longitudinal axis of the chamber. Since this is the coordinate direction for the velocity measurement, such magnification changes would have to be taken into account in determining electrophoretic mobility. The preferred method of astigmatism correction first described above does not affect the magnification along the longitudinal axis of the chamber.

The distance of the eyepiece lens reticle 178 from beam splitting prism 174 is chosen to be equal to the distance between the beam splitter and the grating surface of rotatable disk 50; hence, the image observed through the eyepiece is identical to that imaged onto the surface of the disk except, the image on the disk grating will be limited in the vertical direction by the action of slit 184 in diaphragm 182. Slit 184 is typically 4 mm in the vertical direction and 20 mm in the horizontal direction. Since the optical magnification of the microscope 18 is typically 20 times, the slit corresponds to a field of view in the electrophoresis chamber of about $200\mu \times 1,000\mu$. The reason for restricting the field of view in the vertical direction is that, while the stationary layer is an imaginery cylindrical surface as already mentioned, the focal plane of the objective lens 170 is approximately a plane surface and therefore, points in focus significantly above or below the optic axis 20 would not lie strictly on the stationary layer and thus should not be viewed or measured.

THE MODULATION DISK

In the preferred embodiment, the transparent, modulation disk 50 is 230 mm in diameter, approximately 6 mm thick, and is precisely mounted at its center of rotation on a shaft 186 driven by a motor 188. As best seen in FIG. 1, the grating pattern of opaque lines 52 is provided along a track centered about 100 mm from the center of the disk. Alternate segments of this pattern either transmit or reflect incident light. Typically 3,000 line-pairs are provided along this track, corresponding to a frequency of 5 line-pairs per millimeter at the 100 mm radius. With a magnification of 20, the grating frequency of 5 lp/mm corresponds to 100 lp/mm at the stationary layer in the chamber or a periodicity of $10\mu$. Since clear and opaque line widths are equal, the width of each clear segment is $5\mu$. In order to achieve a reasonably high percentage modulation, the $5\mu$ line width must be equal to or greater than the size of the particle image. For submicron particles, the airy disk has a diameter of approximately $2\mu$ so this condition is fulfilled. In fact, the grating frequency in this case could be even higher. For larger particles, however, (for example, $7\mu$ erythrocytes) the $10\mu$ periodicity appears to be too high. In practice, however, it has been found quite satisfactory because, it is hypothecated, the laser illumination, rather than evenly illuminating the whole particle, merely reflects light from portions of the particle and the reflected image thus appears as one or more smaller particles.

As mentioned above, the disk 50 is precisely mounted on shaft 186, which, in turn, is supported by bearings (not shown). The disk is rotated at a rate of approximately ⅓ revolution per second by motor 188 e.g., a Hearst Model CA with integral gear train. Since there are 3,000 line-pairs for one revolution of the disk and the disk rotates at a rate of ⅓ revolution per second, a ray of light passing through the grating will be interrupted at a rate of 1,000 cycles per second.

If we now consider a stationary colloidal particle in the electrophoresis chamber and consider further that the reflected light from this particle is, in turn, imaged onto the rotating grating, it will be appreciated that the particle image is modulated at a frequency of 1,000 Hz by the action of the disk being driven by motor 188. In actuality, there is not one but many particles migrating in chamber 16, hence, many particle images are simultaneously modulated by the rotating disk grating. The exact number of particle images depends on the concentration of colloidal particles in the chamber and the size of the viewing area defined by the slit. Typically, an ensemble of anywhere from about ten to as many as several thousand particles can be simultaneously imaged through the slit onto the rotating grating of the disk.

THE PHOTOMULTIPLIER MODULE

Still referring to FIG. 5, the aforementioned ensemble of modulated particle images enters the photomultiplier module 56, passes through a red filter 190, and is focused by condenser lens 192 onto the photocathode surface of photomultiplier tube (PMT) 194. The red filter is used to eliminate stray light and for this purpose its bandpass is centered at 6328 A, the same wavelength as the light emitted by laser 10. The condenser 192 allows the use of a small area of the photocathode surface, thus reducing the dark current and associated noise. A PMT such as the EMI 9558 with an S20 response has been found suitable for use with the present invention. Although this tube has a photocathode diameter of 50 mm, the effective diameter can be reduced to approximately 6 mm by means of a conventional magnetic lens assembly 196 suitably supported in front of the PMT photocathode as schematically indicated. Magnetic lens 196 provides about a 10 to 1 improvement in the dark current and associated noise. It should be noted that it is possible to provide even greater sensitivity of cooling the photomultiplier tube. High sensitivity allows the measurement of very small particles, even those having an index of refraction approaching that of the suspending medium. Conversely, where extreme sensitivity is not required, the photomultiplier tube can be replaced by a fully solid-state photo-detector such as the UDT-450 manufactured by United Detector Technology.

When a suitable supply voltage is applied to the PMT, but no electric field exists between the electrodes in electrophoresis chamber 16 (i.e., the colloidal particles are stationary in the chamber ) there results an electrical output signal proportional to the modulated light passing through the grating. This electrical output signal is spectral in nature and contains several frequency components as shown diagramatically in the amplitude frequency domain plot of FIG. 7. Primarily, there is a signal component 200 nominally at 1,000 Hz which is proportional to the brightness and number of particle images within the field of view defined by slit 184. In addition, there is shot noise caused by background illumination as well as thermal noise due to the dark current indicated generally by reference numeral 201. There are additional noise sources at low frequencies indicated generally by reference numeral 199, including amplitude noise on the laser beam itself, 60 and 120 Hz interference from power sources, and finally, doppler noise arising from heterodyne mixing of the laser light on the photocathode surface. However, because the low frequency noise sources produce very little energy at 1,000 Hz they contribute little or no noise component at the nominal 1 KHz modulation frequency.

It will be understood that the PMT output signal primary component will fluctuate slightly in frequency about 1000 Hz due to variations in the speed of motor 188 and other factors. For convenience this signal component will be referred to hereinafter as the center frequency and it will have an exact instantaneous frequency, $f_r$, which latter is nominally 1000 Hz, but which may vary therefrom by several percent.

Consider now the nature of the photomultiplier output signal when the particles move electrophoretically in the chamber, i.e., under the influence of an electric field applied between the electrodes in chamber 16. If one considers first a single colloidal particle moving parallel to the longitudinal axis of the electrophoresis chamber, the particle image will traverse either a greater or lesser number of grating segments on the rotating disk during a given time period compared to when the particle was stationary depending on the direction of the particle movement in the chamber. As a result, the modulation frequency associated with this single particle will be shifted either up or down with respect to the center frequency $f_r$ according to the speed and direction of the colloidal particle. The frequency shift can be given by the following equation:

$$\Delta f = (M\mu E/L) \qquad (3)$$

where: $\Delta f$ is the frequency shift relative to the center frequency, $f_r$, M is the magnification of the objective, $\mu$ is the electrophoretic mobility of the colloidal particle, E is the field strength in volts/cm, and L is the periodicity of the grating. For a typical case, where M=20, $\mu = -2.0 \times 10^{-4}$ cm$^2$ sec$^{-1}$ volt$^{-1}$, E=20 V/cm, and L=0.02 cm, $\Delta f$ is $-4$ Hz. Note that in accordance with the above equation, $\Delta f$ is negative for negatively charged particles when the field strength is positive. This convention will be followed throughout. In this regard, FIGS. 8 and 9 diagramatically illustrate the spectral content of the PMT output signal for an applied field of +20 V/cm and −20 V/cm respectively, relative to the same colloidal particle above. In both FIGS. 8 and 9, it is assumed that the spectra are obtained from a single particle having a mobility of exactly $-2.0 \times 10^{-4}$ cm$^2$ sec$^{-1}$ volt$^{-1}$ hence, the primary spectral components (202, FIG. 8 and 203, FIG. 9) appear as very narrow spikes limited in bandwidth only by the time duration of the measurement and any bandwidth broadening due to random Brownian motion.

FREQUENCY TRANSLATION CIRCUIT

From the preceding description, it is apparent that it is necessary to detect relatively small frequency shifts, on the order of a few cycles, relative to the nominal 1 KHz center frequency ($f_r$). In order to analyze the PMT output signal over this narrow frequency band, the translator circuit 60 of the present invention functions to translate this frequency band to the zero frequency region so that the translated or hererodyned signal can be processed by a conventional real time FFT (Fast Fourier Transform) spectrum analyzer such as a Model 512S, manufactured by Rockland Systems, Inc. Such analyzers provide an analysis band from zero frequency to some selected upper limit and the resolution is typically 1/400 of the analysis range selected. If the analysis range were set to 2 KHz, thereby encompassing the signal at the 1 KHz center frequency, the resolution would be only 5 Hz (2 KHz/400). If it be assumed for the moment that the maximum frequency shift or range of the apparatus will be no greater than ±10 Hz, then there is interest merely in a 20 Hz band centered about $f_r$. The resolution of frequency analysis can be improved very substantially by translating this 20 Hz band of interest so that it falls between zero Hz and 20 Hz. Since the analyzer resolution on this analysis range is now 20/400 or 0.05 Hz, a 100:1 improvement in resolution is gained.

A second function of the translator circuit of the invention is to compensate for the frequency modulation caused by variation in the angular velocity or rotation speed modulation of disk 50. For this purpose, a reference signal having a frequency $f_r$, is generated which is proportional at all times to the instantaneous angular velocity of disk 50 and which is identical to the frequency of the primary spectral component (200, FIG. 7) of the PMT output signal resulting from modulation of the image of a stationary colloidal particle as described above.

In order to generate the reference frequency signal $f_r$, the light emitting diode (LED) 53 and photosensor 57 are provided disposed on opposite sides of the disk 50 as already described in connection with FIG. 1. The LED 53 and sensor 57 are positioned such that the light rays passing therebetween are interrupated by the movement of the grating. Typically, an infrared source is used for LED 53 to minimize the probability of spurious signals entering the photomultiplier detector 56. Although LED 53 and photosensor 57 are shown substantially diametrically opposed to microscope 18 and photomultiplier 56 relative to disk 50 in FIG. 1, this was done merely to prevent obfuscation of the drawing. In practice, LED 53 and photosensor 57 are circumferentially juxtaposed relative to microscope 18 and photomultiplier module 56 so that as nearly as possible the frequency of the output signal of the photosensor is proportional to the instantaneous angular velocity of that portion of the disk grating actually modulating the reflected image viewed by the microscope at any given time.

Turning now to FIG. 11, translator circuit 60 will now be described. It will be understood that since the various individual components of this circuit are known per se, the structural details of these individual components form no part of the present invention. Frequency translator circuit 60 receives both the output signal of the PMT 56 and the output of the photosensor 57 as inputs to a pair of identical bandpass filters 220, 222, respectively. Each filter has a bandpass characteristic centered at 1 KHz and a bandwidth of about 200 Hz. The function of filter 220 is to remove the unwanted previously described low and high frequency noise components from the PMT output signal whereas the use of an identical filter 222 responsive to the output signal of the photosensor assures that the phase of the photosensor output signal will track that of the PMT output signal despite slight changes in the frequency of the former due to slight speed variations of disk 50.

If the output signal of filter 220 which has a primary spectral frequency component equal to $f_r + \Delta f$ were merely mixed or synchronously detected with respect to the output signal of filter 222 which has a frequency equal to $f_r$, a difference signal would result equal to $|\Delta f|$. This difference signal would therefore present an ambiguity since it would be impossible to distinguish between signals shifted up or down in frequency with respect to $f_r$ and therefore, it would be impossible to distinguish between positively and negatively charged particles. However, in accordance with the present invention, the output of filter 222 ($f_r$) together with the 10 Hz output signal derived from crystal-controlled oscillator 224 are applied to a conventional single-sideband modulator (SSB) 226 to produce an offset reference signal output $f_o$ having a frequency equal to $f_r + 10$ or $f_r - 10$ depending upon whether a logic signal is applied to the SSB on line 25 from the Polarity Reverse Logic circuit of controller 32 (FIG. 1). That is, if a logic signal appears on line 25 this corresponds to an applied electric field of positive polarity and SSB 226 will produce the lower sideband e.g., $f_r - 10$, at its output. Likewise, if no logic signal appears on line 25 this corresponds to an applied electric field of negative polarity and SSB 226 will produce the upper sideband, e.g., $f_r + 10$ at its output. In FIGS. 8 and 9, the SSB output signals ($f_o$) are represented by reference numerals 228 and 230, respectively.

The SSB output signal ($f_o$) is then applied along with the output signal of filter 220 ($f_r + \Delta f$) to single sideband demodulator (SSBD) 232 wherein these two signals are heterodyned together to produce a difference or beat frequency signal $f_t$ equal to the difference between the PMT output signal 202 (e.g., $f_r - 4$ Hz) and the SSB offset reference signal 228 (e.g., $f_r - 10$) for an applied electric field that is positive (see FIG. 8); or equal to the difference between the PMT output signal 203 (e.g., $f_r + 4$ Hz) and the SSB offset reference signal 230 (e.g., $f_r + 10$) for an applied electric field that is negative (see FIG. 9). In both cases the beat frequency is equal to 6 Hz and $f_t$ the translator circuit output signal can thus be represented in the frequency domain by reference numeral 204 in FIG. 10.

If the single particle observed had the same magnitude charge or mobility but was positively charged instead of being negatively charged as in the example described above, the PMT output signal would have a primary frequency component equal to $f_r + 4$ Hz when the applied field was positive as indicated by reference numeral 205 in FIG. 8, and would have a primary frequency component equal to $f_r - 4$ Hz in a negative applied field as indicated in FIG. 9 by reference numeral 206. Thus, when these signals are heterodyned with the offset reference signals from SSB 226, the beat frequency signal $f_t$ produced by SSBD 232 is equal to 14 Hz for both the positive applied field (FIG. 8) and the negative applied field (FIG. 9) and the output of the translator circuit, $f_t$, may be represented in the frequency domain by reference numeral 207 in FIG. 10.

It will be appreciated that when SSB 226 is producing its lower sideband $f_r - 10$ (228, FIG. 8) during a positive applied electric field and therefore, there exists no Polarity Reverse Logic signal on line 25, SSBD 232 is demodulating the upper sideband with respect to $f_r - 10$. Accordingly, invertor 234 is provided to produce a "sideband select" logic signal input to demodulator 232 when there is an absence of signal on line 25. Conversely, when there is a signal present on line 25, SSB 226 produces its upper sideband $f_r + 10$ (230, FIG. 9) corresponding to a negative applied electric field, this signal is inverted by invertor 234 and no logic signal is applied to demodulator 232 thus causing the latter to demodulate the lower sideband with respect to $f_r + 10$. In this manner, the demodulator 232 selects the appropriate sideband of interest depending upon whether the applied electric field is positive or negative.

From the foregoing, it will now be apparent that the translator circuit 60 acheives its intended function of heterodyning or translating the PMT output signal from a frequency which varies relative to $f_r$ (nominally 1000 Hz) to a new frequency, $f_t$, which varies within the range of from 0 Hz to 20 Hz relative to the offset frequency obtained from local oscillator 224 namely, 10 Hz, with a variation or shift below 10 Hz indicating that the particle being observed has a negative charge, and with a variation or shift above 10 Hz indicating that the particle being observed has a positive charge. Moreover, not only is the instantaneous frequency $f_t$ independent of the polarity of the applied electric field E impressed across the electrodes of the electrophoresis chamber even though E is reversing its polarity typically every 20 seconds, but $f_t$ is now directly proportional to mobility, since:

$$f_t = 10 + \Delta f \tag{4}$$

Thus, by substituting the value of $\Delta f$ from expression (3) above, (4) may be rewritten as:

$$f_t = 10 + M|E|/L\ \mu \tag{5}$$

or for the particular example employed above $$f_t = 10 + 2 \times 10^4 \mu \tag{6}$$

It is evident, therefore, that the mobility of the charged particle may be directly calibrated as a function of $f_t$, the output signal of translator circuit 60. And although the foregoing operation of this circuit was described with reference to a particular example, this was done merely for the sake of clarifying the presentation. For example, the heterodyned frequency range within which $f_t$ varies relative to the offset frequency can be made larger or smaller by corresponding changes in the frequency of the output signal from local oscillator 224.

REAL TIME FFT ANALYZER

The use of an FFT Real Time Analyzer in accordance with the invention takes advantage of the continuous stream of spectral data produced by translator circuit 60 and converts this data into more meaningful form.

If all particles in a colloidal dispersion had exactly the same charge, one would only have to measure a single particle to completely characterize the whole system. Such behaviour is contrary to experience with sample colloidal dispersions and in almost all cases there are differences in charge among the various particles. Hence, the output signal $f_t$ of translator circuit 60 rather than ideally comprising an infinitely sharp signal of precise frequency corresponding to a single particle, in actual practice, comprises a normal or gaussian distribution of frequencies about a mean frequency corresponding to an ensemble of particles having different charges. In such situations, the mean frequency of this gaussian distributed spectral signal has a value $f_t$ which through expressions (4) and (5) above is related to the mean mobility of the ensemble.

In addition, since as also mentioned above, the magnitude of the output signal of PMT 56 is related to the number of particles being viewed by microscope 18 at any given moment, a histogram of the charge/mobility distribution vs. relative number of particles may be obtained from $f_t$, the spectral output signal of translator circuit 60, by utilizing the Real Time FFT Analyzer 61 (FIG. 1). A facsimile of such a histogram as it might appear on the CRT display of the Analyzer is shown in FIGS. 14 and 15 represented by reference numeral 240 and corresponding to a mean frequency component at 6 Hz and to a mobility of $-2.0 \times 10^{-4}$ cm$^2$ sec$^{-1}$ volt$^{-1}$, i.e., the same as that for the exemplary single particle described above. Again, however, it is emphasized that in practice, it is a mean frequency component of a gaussian distribution relating to a charge distribution of many particles that is depicted by a histogram such as that represented by reference numeral 240 in FIG. 14.

As indicated above, the resolution of the Analyzer is 0.05 Hz on the 20 Hz analysis range. Therefore, in order to actually obtain this resolution the input signal must be present for a time period equal to the reciprocal of the resolution or 20 seconds. The desired resolution therefore is one factor which limits the minimum rate at which the polarity of the electric field E can be reversed. Thus, in generating the histogram 240, the Analyzer examines the translator output signal throughout the frequency range from 0 Hz to 20 Hz in 400 discrete steps each corresponding to a 0.05 Hz resolution element as diagramatically represented in FIG. 15. In this regard, it should be noted that the effect of changing the concentration of colloidal particles results in a corresponding change in the number of particles corresponding to each resolution element (and all the others as well). The rms value of the signal in each resolution element is not linear with the number of particles but instead increases only as the square root of the number of particles. Thus, if the histogram presentation is to be proportional to the number of particles in each resolution element, then the vertical axis display of the analyzer should correspond to the voltage$^2$ or power spectrum instead of the voltage spectrum.

Furthermore, histogram 240 obtained for a single 20 second sample will be somewhat limited in significance by the fact that a finite number of particles will have been measured, and even that measurement will be contaminated somewhat by spurious noise. A more significant histogram from a statistical viewpoint can be obtained by averaging the data over many cycles of the electric field reversal, typically, 8-32 separate 20 second samples being averaged to obtain a histogram of sufficient quality.

It should be noted finally that the usefulness of the averaging feature depends upon obtaining statistically independent input samples. However, if the electric field across the electrodes in the electrophoresis chamber is reversed once every 20 seconds, the same particles may repeatedly pass back and forth across the viewing slit. If this was indeed the case, the statistical significance of the histogram would not improve substantially with increasing number of averages because the same limited number of particles would be repeatedly measured. The foregoing is overcome to a great extent in the present invention because there is some settling of larger particles in the chamber. By settling is meant displacement in the vertical direction under the influence of gravity. This settling phenomenon tends to replace a certain number of particles with new ones as the measurement proceeds. Secondly, by proper selection of the magnitude of the applied electric field strength it is possible to control the convection currents in the chamber so as to provide a very small vertical motion of particles at the stationary layer to add to the settling velocity and thus add to the particle turnover, but without causing such convection currents to produce any velocity component in the horizontal direction and thereby produce errors in the measured electrophoretic mobility.

When sufficient data has been obtained, the electric field across the electrodes in the chamber may be turned off and the histogram spectrum 240, which has been continuously observed on the CRT display of the Analyzer may be plotted on conventional X-Y recorder 63 to produce a permanent record of the measurement.

In addition to recording the histogram spectra itself, it is sometimes convenient to also plot, using a second pen in the recorder the integral of the spectra represented by reference numeral 242 in FIG. 14. By observing the point 244 at which the integral reaches half scale, it is a simple matter to define this point as that corresponding to the center or mean value of the mobility spectra. Hence, in the exemplary histogram 240 of FIG. 14, the mean mobility is related to the mean frequency of the histogram spectrum which is indicated as 6 Hz.

THE FREQUENCY TRACKER

As will be understood by those skilled in the art, the use of the Real time Analyzer to develop histograms of the output spectra of translator circuit 60 is extremely valuable in analyzing the charge distribution of a sample colloidal dispersion in electrophoresis chamber 16. However, in situations where it is merely necessary to obtain a measure of the mean mobility of the sample dispersion the frequency tracker circuit 65 may be employed in lieu of the Real Time Analyzer.

Thus, turning now to FIGS. 12 and 13, the frequency tracker 65 according to the present invention will now be described. As in frequency translator circuit 60, previously described, the individual components or blocks of the frequency tracker circuit 65 are well known and their structural details form no part of the present invention. The output spectra of translator circuit 60 which has a mean frequency $f_t$ is applied simultaneously to a pair of multipliers 250 and 252. A voltage controlled oscillator 254 has its frequency output divided by a factor of 100 in divider 256 and the resulting signal which has a frequency $f_{LO}$ is then applied to 90° phase splitter 258. The phase splitter 258 in turn, produces a pair of outputs which are always in quadrature with each other and therefore these signals may be represented as sin $f_{LO}$ and cos $f_{LO}$, respectively. The phase splitter output signals are then applied respectively to multipliers 250 and 252 to produce a pair of quadrature related beat frequency or difference signals which may be represented as sin $f_t - f_{LO}$ and cos $f_t - f_{LO}$, respectively. The latter signals are then applied to a frequency discriminator 260 which has a characteristic as shown in FIG. 13 and thus, is adapted to generate an error current $i_e$ whose magnitude and polarity are proportional respectively to the difference and polarity of $f_t - f_{LO}$. That is, if $f_t > f_{LO}$ then $i_e$ will be negative in polarity, and if $f_t < f_{LO}$ then $i_e$ will be positive in polarity. The error current $i_e$ is then fed to integrator 262 which in response thereto produces an output voltage which is applied to the voltage controlled oscillator 254 for controlling the frequency of the output thereof. The voltage controlled oscillator has an increasing frequency characteristic for an increasing voltage input. Since the integrator 260 will produce a positive output voltage for a negative input and vice versa, a negative error current $i_e$ at the output of discriminator 260 (i.e., $f_t > f_{LO}$) will cause the voltage controlled oscillator output frequency to increase until a null is reached and $f_{LO} = f_t$ = mean frequency of translator circuit output signal. After a predetermined time interval, say 5-10 seconds, for example, at the end of which the foregoing null condition will be established, computing means 264 which may comprise a Motorola Model 6800 Microprocessor, feeds an appropriate signal to a control network 266 which narrows the bandwidth of the discriminator characteristic so that $f_{LO}$ can more precisely track slight changes in $f_t$.

Thus far, the frequency tracker circuit 65 is known per se. However, in accordance with the present invention there is provided in the feedback loop of integrator 262 a first capacitor 226 in series with switch 268, and a second capacitor 270, identical to first capacitor 266, in series with switch 272, substantially as shown. A control relay 274 coupled to switches 268, 272 is connected to line 27 and thus receives the Polarity Reverse Logic signals from controller 32 (see FIG. 1). When a signal is present on line 27 signifying a negative electric field applied across the electrodes in chamber 16 relay 274 is energized to a first position wherein switch 268 is closed completing the integrator 262 feedback loop through capacitor 266. Conversely, when there is no signal present on line 27, this signifies a positive applied electric field and relay 274 becomes deenergized, thus opening switch 268, and closing switch 272, whereupon capacitor 270 rather than capacitor 266 is in the feedback loop of integrator 262.

In addition, there is provided between the output of voltage controlled oscillator 254 and computing means 264, a counter 276 which accumulates a count in response to each output pulse in the output waveform of oscillator 254, which accumulated count is continuously applied to computing means 264.

In operation, assume an electric field of positive polarity is applied across the electrodes in the electrophoresis chamber for an initial period of time (e.g. 20 seconds). During the first 5-10 second portion of this period, the tracker loop acquires the input signal having a mean frequency $f_t$ and then the computing means 264 causes the frequency discriminator to switch to a narrower band through control network 266. This eliminates unwanted noise which would degrade the mean mobility measurement. The same acquisition and switch to a narrower band produce is repeated during a second period of time corresponding to a negative electric field. Although during these first two cycles, counter 276 is accumulating a count in response to the output of oscillator 254 this data is disregarded and the counter is reset. Now assume that the tracker has acquired the input signal $f_t$ and another cycle or time period begins with an electric field of positive polarity being applied across the electrodes in the chamber. As the tracker loop tracks the input signal $f_t$, counter 276 continues to accumulate its count. At the end of the period through which the positive electrid field is applied and immediately prior to reversal of the electric field polarity, the accumulated count is stored in computing means 264 and a voltage appears across capacitor 270 through closed switch 272 which voltage is proportional to the mean frequency $f_t$ since the tracker loop is in a null condition. The electric field applied across the electrodes in the electrophoresis chamber now changes its polarity (i.e., becomes negative), relay 274 becomes energized causing switch 272 to open and switch 268 to close, and the counter continues to accumulate the count in response to the oscillator output. At the end of this period and immediately prior to still another reversal of the polarity of the applied electric field, the count accumulated by counter 276 is again stored in computing means 264, the tracker loop is at a null condition, and the voltage appearing across capacitor 266 should again be proportional to the mean frequency $f_t$; that is, if the apparatus is operating properly, the count accumulated during the period of one polarity of applied electric field should approximately be equal to the count accumulated during the period of the other, reversed polarity of electric field. The foregoing is then repeated for a sufficient number of additional cycles as may be required to accumulate data of a desired accuracy e.g., 4-16 complete cycles where each cycle includes both positive and negative applied electric fields.

It is emphasized that the provision of two independent capacitive feedback loops around integrater 262 in accordance with the present invention, renders it possible to measure mobility data (by accumulating a count in counter 276) corresponding to applied electric fields of one polarity, to independently measure such data corresponding to applied electric fields of an opposite polarity, and then to average the data separately over any number of successive cycles. This is quite significant because the separately obtained data can now be used to test the system if it is not operating properly and to determine the type of error responsible. For example, two common forms of error which produce erroneous measurements in electrophoresis systems comprise drift due to small leaks, and gassing due to electrolysis at one or the other electrode. Now assume that one of these error sources is present and that as a result, the average count accumulated during N cycles corresponding to one polarity of applied electric field is different from the average count accumulated during the same number of cycles corresponding to the opposite polarity of applied electric field and that therefore, a test is in order to determine the nature of the error source. In order to conduct the test in accordance with the invention, the apparatus is then operated for N cycles, however, the electric field strength during the test is reduced to zero. Since gassing will not occur in the absence of an applied electric field between the electrodes in the chamber, a difference between the average counts corresponding to the N cycles of measurement associated with each capacitive feedback loop will indicate that the error is due to drift and must be as a result of a small leak in the system. If, on the other hand, there is no difference between the average counts corresponding to the N cycles of measurement associated with each capacitive feedback loop under zero field strength conditions then the error must be due to the presence of gas bubbles, not to leakage.

While such errors are to a great extent automatically corrected by the fact that the polarity of the applied electric field is reversing periodically and thus the errors will not affect the accuracy of mean mobility measurements, it is desirable to correct these errors in order to maintain a high degree of resolution when a spectrum analyzer is being employed to generate a mobility histogram, for example.

Another important advantage of the frequency tracker circuit of the present invention is its ability to provide a highly accurate measure of the mean mobility by averaging the accumulated count over a series of many cycles of polarity reversals. The mean mobility can be derived as follows. After acquisition is complete $$f_{LO} = f_t \text{ and } f_{VCO} = 100 f_t \tag{7}$$

where $f_{VCO}$ is the output of oscillator 254. The number accumulated during the time that one polarity of electric field is applied is referred to as COUNT and is simply the product of $f_{VCO}$ and the time $T_m$ for that period $$COUNT = 100 \cdot f_t \cdot T_m \tag{8}$$

Thus, substituting (8) into (5) we get $$COUNT = 100 \, T_m \left[ 10 + \frac{M|E|}{L} \mu \right] \tag{9}$$

rearranging (9) yields $$\mu = \frac{L}{M|E| \cdot 100 \, T_m} [COUNT - 1000 \, T_m] \tag{10}$$

For the typical case given previously where $M|E|/L = 2 \times 10^4$ and for $T_m = 20$ seconds $$\mu = \frac{1}{4 \times 10^7} [COUNT - 20,000] \tag{11}$$

thus, if COUNT is zero $$\mu = -5 \times 10^{-4} \, cm^2 \, sec^{-1} \, volt^{-1} \tag{12}$$

or, if COUNT is 20,000

$$\mu = 0 \tag{13}$$

or, if COUNT is 40,000
$$\mu = +5 \times 10^{-4} \, cm^2 \, sec^{-1} \, volt_{-1} \tag{14}$$

It will be observed therefore that in similar fashion to the mobility histogram described above in connection with FIG. 14 the mobility range scale is $\pm 5 \times 10^{-4} \, cm^2 \, sec^{-1} \, volt^{-1}$.

OPERATION OF APPARATUS

Before proceeding with a detailed description of the operation of the apparatus of the present invention, it will be helpful to initially describe certain procedures employed in calibrating the apparatus.

As is well known, if the electrophoretic velocity measured by the apparatus is to be accurate, the measurement must be made at the stationary layer. At any other location, the particle velocity may contain an electro-osmotic velocity component due to a charge or charges on the surfaces of the electrophoresis chamber. As already explained above, for a cylindrical chamber, the stationary layer is an imaginary cylindrical surface having a radius of 0.707 times the radius of the inside bore of the chamber. Thus, to focus at the stationary layer in chamber 16, the bright field illuminator as described previously in connection with FIG. 1, is employed and one first focuses at or on the inside front wall of the chamber, then the inside back wall, recording the setting of micrometer 120 at both points. The calibration marks 80 previously described, on the inside bore of the chamber are used for this purpose. One then calculates the location of the stationary layer taking into account any optical distortions present in the system. This procedure is well known to those skilled in the art.

At the stationary layer, the observed frequency shift $\Delta f$, in accordance with expression (3) above, is directly proportional to the electrophoretic mobility, the magnification of the objective, the electric field strength, and inversely proportional to the periodicity of the grating.

The magnification M can be determined by using the accurately spaced marks 80 on the inside of the electrophoresis chamber and measuring the magnification through the calibrated eyepiece reticle 178.

The periodicity of the grating can be accurately controlled during manufacture since it is ruled on a precision engine under very carefully controlled conditions. However, the periodicity of the rotating disk 50 depends upon the radial distance of the point of observation from the center of the disk. Typically, the periodicity of the disk is determined at a distance of 100 mm from the rotation center of the disk. To facilitate calibration, a very fine line 280 is disposed at this 100 mm radius circumferentially of the disk as shown in FIG. 1. As part of the calibration procedure, one visually checks that the narrow slit 184 is centered with respect to this circumferential line 280.

In order to increase the accuracy of the measurements made by the apparatus of the invention, the value of the electric field should be as precisely controlled as possible. A common procedure for accomplishing this is to apply a constant voltage across the electrodes and to calculate the applied field by dividing the applied voltage V by an "effective length" $L_e$.

Thus, $E = V/L_e$ (15)

For example, if the applied voltage is 40 V and the effective length is 2 cm, the field strength is therefore 20 V/cm. The effective length may be measured using a calibrating fluid such as 0.01 M KCl and can be calculated by the following expression:

$$L_e = AK \quad (16)$$

where A is the cross-sectional area of the chamber and K, the chamber conductivity constant, is defined by the following expression:

$$\sigma = K(I/V) \quad (17)$$

where:
- $\sigma$ = conductivity of the fluid
- I = current through the chamber
- V = voltage across the chamber The value of K for a particular chamber is normally determined using equation (17) and a fluid of known conductivity such as the 0.01 M KCl referred to above. The I/V ratio is typically measured on a Wheatstone bridge, usually at a frequency of at least 60 Hz in order to avoid polarization errors which become significant below 60 Hz. The constant A is determined optically by measuring the diameter of the chamber while it is immersed in water using the calibrated focus adjustment mechanism on a high quality microscope. The area A is then simply $\pi D^2/4$ where D is the measured inside diameter.

The foregoing procedure for controlling the field strength E suffers from several disadvantages. In the first place, the measurement of electrophoretic mobility, as we have seen, may require the applied field to be held constant for as long as 20 seconds. During this time period, electrode polarization will tend to introduce an increasing voltage drop across the electrode-fluid interfaces thereby reducing the field strength E at the point of measurement. Secondly, reaction products occurring at the electrode surfaces will tend to produce conductivity changes in the electrode chambers thus causing still further changes in field strength and consequently, measurement errors.

In practicing the present invention, the field strength may be controlled more accurately by utilizing the relation:

$$E = I/A\sigma \quad (18)$$

where I is the current through the chamber and A and $\sigma$ refer respectively to the cross-sectional area and conductivity within the region of the chamber defined by the field of view of the microscope. It should be noted that the conductivity in this region is not affected by the reactions taking place at the electrodes (provided that the particular polarity of the electric field is not applied for too long a period such that the reaction products reach the mid point of the chamber).

Since A and $\sigma$ can be accurately measured, as described previously, it follows that the field strength E can be controlled accurately by calculating an appropriate current $I_m$ by means of equation (18) and operating in a constant current mode. In this manner, the polarization effects and conductivity changes in the vicinity of the electrodes tend not to change the value of the field strength in the area of measurement.

As indicated above, a typical applied electric field strength would be 20 V/cm. In practice, the selected field strength is a function of three factors. First, the applied field should not be so great that it causes Joule heating to the extent that turbulence is produced in the chamber thus rendering compensation for convection currents inadequate. Secondly, the applied voltage should not be so minimal that bandwidth broadening due to Brownian motion or the resolution limit of the Real Time Analyzer mask the desired resolution in the mobility histogram. Finally, it will be found convenient to select the field strength so as to obtain a workable scale factor between mobility (or zeta potential) and the frequency shift in Hz. Thus, in the example discussed above, when the field strength was selected to be 20 V/cm the resulting scale factor produced a mobility range of $-5$ to $+5$ ($10^{-4}$ cm$^2$ sec$^{-1}$ volt$^{-1}$) corresponding to a frequency shift range of 0 Hz to 20 Hz as shown in FIG. 14. Once a suitable field strength is selected, taking into account the previous factors, one calculates the appropriate current $I_m$ for making the measurement using equation (18) and this value is entered into controller 32 for supplying a current magnitude instruction on line 35 to constant current source 30.

Referring to FIG. 1, the apparatus is then employed to make a mobility mesurement as follows. The first step is to empty chamber 16 and refill it with a fresh sample colloidal dispersion. This is accomplished by opening valve 36 to allow the chamber to vent, opening valve 40 and turning pump 42 on. As a result, the contents of the chamber are emptied into waste container 48. Next, valve 36 is closed causing sample dispersion 44 in container 46 to be aspirated through input pipette 34. It is also desirable to aspirate a few air bubbles to help flush any residue from the chamber. Such bubbles can be generated by momentarily withdrawing the pipette tip one or more times from sample container 46. When the chamber is filled, the peristaltic pump 42 is stopped, valve 40 is closed and valve 36 is opened. The purpose of valve 36 is to provide an air vent to the chamber such that back pressures created by vibration or other means are not transmitted by the sampling tube 34 into the chamber, thus causing false migration of the colloidal particles.

The filling of the chamber can be automated by feeding into it a succession of sample dispersions using air bubbles to separate each sample. When this is done, it may be desirable to provide two bubble sensors (not shown) located on opposite ends of the chamber just outside of valve 40 and 36 respectively. The purpose of such sensors is to insure that the pump is not stopped while a bubble is in transit through the chamber. Such bubble sensors are commercially available and consist of a light source, such as an LED, and a photosensor so arranged that the difference in refractive index between the air bubble and the suspending material causes a sufficient difference in the light energy picked up by the photosensor to generate a control signal in response to the presence or absence of a bubble passing the sensor. The control signal may then be used to control the operation of pump 42.

It will be appreciated further that a multitude of sample containers 44 might be employed mounted on a carousel or "lazy susan". Such equipment may be operated automatically to pass a different sample through the chamber after a predetermined time interval and is commercially available from Technicon Corporation, for example. Alternatively, the sample container 44 might be replaced by an automatic sampling module which provides a direct connection to a process being controlled or monitored and continuously feeds successive samples through chamber 16.

In order to make the mobility measurement, it is merely necessary to cause the reversing polarity electric field to be impressed across the electrodes in the electrophoresis chamber for a suitable number of cycles to obtain a satisfactory histogram, or if employing a frequency tracker, to obtain a reading of the mean mobility. After sufficient data has been obtained, the current source is denergized, a new sample dispersion is fed into the chamber, and the process repeated.

EXTENSIONS OF THE BASIC APPARATUS

From the foregoing, it is evident that the present invention relates to a significantly improved automatic apparatus for measuring the electrophoretic mobility or zeta potential of suspended particles.

Since the apparatus of the invention is capable of operating automatically without the involvement of a human operator once it has been properly set up and calibrated as explained above, it is possible to employ the apparatus of the invention as an element in a automatic control system for controlling an industrial process requiring continuous and/or periodic adjustment of zeta potential. For example, with regard to the wet end portion of the process for manufacturing paper, it is well known that improved wet strength, higher retention of chemicals, improved drainage permitting speed increases, or alternatively, a reduction in energy consumption, and reduced B.O.D. levels of effluent providing easier waste treatment can be achieved by controlling zeta potential. Thus, the apparatus of this invention can be employed in a paper making wet end chemistry control system wherein samples of the white water or headbox stock, for example, are continuously fed into chamber 16 and the apparatus automatically measures the electrophoretic mobility and/or zeta potential of each sample in the manner explained above, and by way of a computer or microprocessor continuously compares the measured values to a set of preprogrammed values. Should there be a difference between the measured values and the programmed values, the computer will furnish an error signal to a controlled element for properly adjusting the chemical properties of white water, headbox stock, etc. and thus, the zeta potential thereof, until the computer senses via the apparatus of the invention that the zeta potential or electrophoretic mobility being continuously measured has returned to its programmed value.

Likewise, the ability of the disclosed apparatus to measure the zeta potential of small sample volumes, and its ability to rapidly feed these sample volumes through the chamber in succession without cross-contamination enables the apparatus to be especially useful as a diagnostic bio-medical instrument capable of analyzing a wide variety of biological materials.

Although preferred embodiments of the invention have been fully disclosed above as required by statute, it is apparent that many additional modifications may be made to the basic apparatus described herein without departing from the principles of the invention. For example, by inserting a conventional dove prism (not shown) between beam splitter 174 and the ruled grating on disk 50 (see FIG. 5) one can, by suitable rotation of the dove prism, rotate the image projected onto the grating by exactly 90°. The horizontal velocity component of the image modulated by the rotating grating will now correspond to a vertical velocity component of the particle in the chamber itself. Hence, the same apparatus can be used to measure both electrophoretic and settling velocities. If only a frequency tracker is used, one can only measure mean settling rates. If a sprctrum analyzer is used, settling velocity histograms may be obtained in a manner similar to that described above to obtain mobility histograms. The effect of gravity takes the place of the applied electric field in producing the motion to be measured, and since gravity acts in one polarity, the polarity switching signal is kept in one state.

Furthermore, if one knows the specific gravity $\sigma$ of the colloidal particles and the specific gravity $\sigma_o$ and viscosity $\eta$ of the medium, it is also possible to determine the size distribution of a colloidal dispersion by utilizing such a settling velocity histogram and Stokes Law which states that:

$$d^2 = \frac{18\eta\nu}{(\zeta - \zeta_\sigma)} \times 10^8 \qquad (19)$$

where:
$\theta$ = velocity of settling particle
and
d = diameter of the particle This method would be suitable for measuring relatively large-sized particles, e.g. $>0.5\mu$.

Another technique which can be employed for smaller-sized particles utilizes an inverse relationship between bandwidth broadening due to Brownian motion and particle radius given by the following equation:

$$BW = \frac{4\pi DM^2}{L^2} \qquad (20)$$

Where: BW is the bandwidth broadening in Hz due to Brownian motion, D is the diffusion constant associated with the particles, M is the magnification of the microscope objective, and L is the periodicity of the grating.

For aqueous systems:

$$D = \frac{2.15 \times 10^{-13}}{a} \text{ cm}^2 \text{ sec}^{-1} \qquad (21)$$

where: a is the radius of the colloidal particles. For a typical case; M=20, L=0.02 cm, and for human erythrocytes, a=3.5 microns. The resulting spectral broadening under these conditions is approximately 0.008 Hz which referring to equation (6) we note corresponds to a mobility broadening of only $0.004 \times 10^{-4}$ cm$^2$ sec$^{-1}$ volt$^{-1}$. The broadening due to Brownian motion puts a limit on the histogram resolution that can be obtained with the spectrum analyzer but we see that for human erythrocytes the broadening is less than the basic resolution of the analyzer. However, if the particle radius is 0.035 microns instead of 3.5μ the bandwidth broadening would amount to 0.8 Hz which is easily detected with an analyzer resolution of 0.05 Hz. The bandwidth broadening can be measured by simply measuring the half width of the spectrum obtained with the electric field set to zero. The mean radius of the particles is then calculated using equations (20) and (21). The advantage of this type of measurement over the settling type measurement is that one does not have to know the specific gravity of the colloid. The disadvantage is that only mean particle size is obtained and therefore the technique is primary applicable to those particles having a reasonably narrow size distribution.

In addition to particle size, the measurement of the turbidity of a colloidal suspension may be obtained by the present invention, since the dc output from the PMT is directly proportional to the turbidity of the sample dispersion in the electrophoresis chamber. For samples having a fairly low concentration of particles, it is desirable to defocus the laser optics assembly so as to provide a thicker curtain of light since for a turbidity measurement it is not necessary that any of the illuminated particles be in focus.

Although in the preferred embodiments detailed above, the use of a laser illumination source is called for to provide an intense source of light in the immediate vicinity of the stationary layer, this is not critical to the present invention. For large-sized particles, a conventional light source may be used providing there is adequate contrast. Similarly, various phase contrast schemes for illumination can be employed.

In addition, since a monochromatic illumination source (laser) is not required, the particles in the chamber may be fluorescent tagged, and blue and ultraviolet light sources may be employed for excitation of the tagging phosphors. When this is done, the bandpass filter employed with PMT 56 will be changed to one that rejects the phosphor excitation frequencies and passes only the flourescing wavelengths.

Likewise, although the chamber described herein is a cylindrical chamber well suited to a wide variety of applications other shapes may be employed instead. Thus, for example, in applications where the particles settle so rapidly through the field of view that adequate resolution cannot be obtained, a rectangular cell may be used since the latter provides a stationary layer which is an imaginery plane surface (as opposed to a cylindrical one) and thus the focal plane of the objective coincides with the stationary layer over a greater vertical distance.

Finally, although a ruled grating on a rotating transparent disk is entirely satisfactory to modulate the reflected particle images viewed by the microscope, it will be appreciated that the moving grating may be supported by other means such as an endless tape, rotating cylindrical drum, and so on.

As used hereinabove, the term "mobility" means electrophoretic mobility unless indicated to the contrary.

Accordingly, it is desired that the present invention be limited only by the true spirit and scope of the appended claims.

What is claimed is:

1. A chamber for use in applying an electric field comprising
    an elongate tubular member and a conductive layer bonded to a portion of the surface of said tubular member serving as an electrode, said conductive layer being bonded to a portion on the interior surface of said tubular member, and
    wherein said conductive layer includes a further portion on the exterior surface of said tubular member, said conductive layer further portion being electrically connected to said first-mentioned conductive layer.

2. The invention of claim 1 wherein said first-mentioned conductive layer and said conductive layer further portion are disposed adjacent one end of said elongate tubular member and are in at least partial overlapping relation with each other.

3. The invention of claim 1 wherein said conductive layer comprises a cylindrical surface disposed coaxially with respect to the axis of said elongate tubular member.

4. The invention of claim 1 further including a thin layer of silicone disposed on said tubular member and said conductive layer to reduce the surface charge thereon.

5. The invention of claim 1 wherein said conductive layer comprises platinum.

6. The invention of claim 5 further comprising a layer of palladium disposed on said layer of platinum.

7. An electrophoresis chamber comprising an elongate tubular member and a pair of spaced electrodes for applying an electric field parallel to the axis of said chamber, wherein at least one of said pair of spaced electrodes comprises a thin electrically conductive layer on said tubular member, said layer having a portion on the exterior of said tubular member and another portion on the interior of said tubular member, said exterior and interior portions being electrically connected to each other and being in at least partial overlapping relation to each other.

8. The apparatus of claim 7 wherein said tubular member includes at least one globular cavity intermediate the ends thereof, and wherein the inner terminal portion of said interior portion of said layer is substantially hemispherically shaped and disposed on a corresponding portion of the interior surface of said globular cavity.

9. The apparatus of claim 8 wherein the center of curvature of said substantially hemispherically shaped layer inner terminal portion is located on said axis of said tubular member and lies in an imaginery transverse plane passing through the juncture of said tubular member between the globular cavity and the portion of the tubular member distal from said one end portion thereof.

10. The apparatus of claim 7 wherein said thin conductive layer comprises platinum.

11. The apparatus of claim 10 further comprising a layer of palladium disposed on said layer of platinum at least in the region of said inner terminal portion.

12. The apparatus of claim 7 wherein said tubular member has a circular shaped transverse cross-section.

13. The apparatus of claim 7 wherein said tubular member has a pair of opposed ends, said pair of electrodes being disposed on each of said ends respectively, said tubular member being mounted on a support member with the axis of said tubular member being horizontal, said support member defining enclosure means for enveloping a portion of said tubular member intermediate said opposed ends thereof, said support member including an inlet and an outlet communicating with the interior of said enclosure such that a constant temperature fluid may be circulated through said enclosure interior via said inlet and said outlet and maintain said portion of said tubular member intermediate the ends thereof at a constant temperature.

14. The apparatus of claim 13 wherein said support member includes an opening in one side thereof adapted to receive the objective lens housing of a microscope such that the optical axis of said microscope intercepts said tubular member intermediate portion, and a flexible sealing water-tight member connected between said support member one side and said microscope lens housing.

15. The apparatus of claim 14 wherein said microscope objective lens housing is mounted on another support member, said first-mentioned support member and said another support member being selectively movable relative to each other whereby said microscope objective lens housing may be selectively focused relative to different portions of said tubular member intercepted by said microscope optical axis.

* * * * *